(12) United States Patent
Yang

(10) Patent No.: US 6,865,246 B2
(45) Date of Patent: Mar. 8, 2005

(54) TRUE 3D CONE-BEAM IMAGING METHOD AND APPARATUS

(75) Inventor: Xiaochun Yang, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 16 days.

(21) Appl. No.: 10/400,344

(22) Filed: Mar. 26, 2003

(65) Prior Publication Data

US 2003/0202637 A1 Oct. 30, 2003

Related U.S. Application Data

(63) Continuation-in-part of application No. 10/256,727, filed on Sep. 26, 2002.
(60) Provisional application No. 60/325,055, filed on Sep. 26, 2001.

(51) Int. Cl.[7] ................................................ A61B 6/03
(52) U.S. Cl. ............................. 378/4; 378/15; 378/901
(58) Field of Search ........................... 378/4, 8, 15, 19, 378/901

(56) References Cited

U.S. PATENT DOCUMENTS

| | | |
|---|---|---|
| 5,592,523 A | 1/1997 | Tuy et al. |
| 5,625,660 A | 4/1997 | Tuy |
| 5,805,659 A | 9/1998 | Tam |
| 5,926,521 A | 7/1999 | Tam |
| 5,933,517 A | 8/1999 | Grangeat et al. |
| 5,999,587 A | 12/1999 | Ning et al. |
| 6,219,441 B1 | 4/2001 | Hu |
| 6,275,561 B1 | 8/2001 | Danielsson |
| 6,285,733 B1 | 9/2001 | Proksa et al. |
| 6,292,525 B1 | 9/2001 | Tam |
| 6,411,670 B1 | 6/2002 | Besson |
| 6,574,299 B1 | 6/2003 | Katsevich .................... 378/14 |

FOREIGN PATENT DOCUMENTS

| | | |
|---|---|---|
| EP | 0 292 402 | 11/1988 |
| WO | WO 99/01066 | 1/1999 |
| WO | WO 01/06931 | 2/2001 |
| WO | WO 01/60236 | 8/2001 |

OTHER PUBLICATIONS

Tang and Ning (2001) "A cone beam filtered backprojection (CB–FBP) reconstruction algorithm for a circle–plus–two–arc orbit" Med. Phys. 28(6):1042–1055.

*Primary Examiner*—David V Bruce
(74) *Attorney, Agent, or Firm*—Robert J. Sayre; Mintz, Levin, Cohn, Ferris, Glovsky and Popeo, P.C.

(57) ABSTRACT

A three-dimensional image of an object scanned with a plurality of cone-beam projections from a number of source positions is reconstructed using a method wherein intermediate transform functions are obtained from two-dimensional images of radiation attenuation in the scanned object. The intermediate transform functions are then filtered over a set of parallel planes using a moving-frame technique. The second-order radial derivative of the Radon transform can then be backprojected to generate an intermediate, locally-reconstructed, three-dimensional image. After repetition of this process, the plurality of intermediate, locally reconstructed, three-dimensional images are summed to obtain an ultimate, reconstructed, three-dimensional image of the object. In particular embodiments, the source and detector are displaced along helical paths and radiation scans of the object are taken at multiple positions along the paths.

24 Claims, 17 Drawing Sheets

TRUE 3D CONE-BEAM IMAGING METHOD AND APPARATUS

RELATED APPLICATION

This is a request for a filing of a continuation-in-part application under 37 C.F.R. 1.53(b) of U.S. Ser. No. 10/256,727, filed Sep. 26, 2002, which is incorporated herein by reference. In addition, this application claims priority to Provisional Application 60/325,055, filed Sep. 26, 2001, also incorporated herein by reference.

BACKGROUND

Cone-beam computerized tomography (CT) reconstructs the absorption function of a three-dimensional object from a set of cone-beam projections. Such a system uses an area detector to receive rays emitted from an X-ray point source and attenuated by partial absorption in the object through which they pass. As in traditional (i.e., planar) CT, the source 10 and the detector 12 are placed on opposite sides of the object 14 being scanned (see FIG. 1). Rays contributing to an image on the detector surface form a cone with the X-ray source 10 at the apex. From the X-ray radiance value recorded at a point on the area detector 12, one can compute the integral of attenuation along the ray from the X-ray source 10 to the given point on the detector 12.

As the source-detector 10/12 pair undergoes a simultaneous rotation and translation around the object 14, a plurality of two-dimensional cone-beam images projected from various source positions can be acquired and used to reconstruct the distribution of absorption inside the three-dimensional object 14. The curve followed by the radiation source relative to the scanned object is called the source orbit or the scan path.

Compared to the traditional slice-at-a-time tomographic machine, the cone-beam CT offers faster scans, higher patient throughput, significant reduction in X-ray dosage, and isotropic resolution. It has a great potential to be applied to a wide range of medical and industrial applications.

Radon's 1917 inversion formula (Johann Radon "Über die Bestimmung von Funktionen durch ihre Integralwerte längs gewisser Mannigfaltigkeiten," *Ber. Verh. Sächs. Akad. Wiss. Leipzig. Math. Nat. Kl.*, Vol. 69, pp. 262–277, 1917) plays an important role in understanding the cone-beam reconstruction problem. The building blocks of the three-dimensional Radon inversion formula are planar integrals. We can write a plane in $\mathbb{R}^3$ as $$L_{l,\beta} := \{x \in \mathbb{R}^3 | x \cdot \beta = l, l \geq 0, \beta \in S^2\}, \quad (1)$$

where $\beta$ is the unit normal of the plane and l is the perpendicular distance of the plane from the origin. The Radon transform of a function $f$ on $\mathbb{R}^3$ is defined as the set of integrals of $f$ over all the planes in $\mathbb{R}^3$ which can be expressed as a function of two parameters (l and $\beta$):

$$Rf(l, \beta) := \int_{x \in \{x | x \cdot \beta = l\}} f(x) dx. \quad (2)$$

The Radon inversion formula is given by:

$$f(x) = -\frac{1}{8\pi^2} \int_{S^2} \left. \frac{\partial^2 Rf(l, \beta)}{\partial l^2} \right|_{l=x \cdot \beta} d\beta, \; x \in \Omega, \quad (3)$$

in which, $S^2$ denotes the two-dimensional unit sphere in $\mathbb{R}^3$ and $\Omega$ denotes the support of $f$. The integral in Eqn. (3) over $S^2$ is the backprojection operator; it integrates over all the planes passing through x. The integration sphere is therefore called the backprojection sphere with its center at x, denoted by $S_x^2$ (x is considered as an index). It is clear that the points on $S_x^2$ represent the unit normals of all the planes through x.

To recover the function value at point x, $R''f(l,\beta)$ is obtained on all or almost all planes passing through x. In cone-beam reconstruction, however, planar integrals are not available from the cone-beam data because rays diverge from the point source inside each projection. Hence, the Radon formula (Eqn. (3)) can not be immediately employed.

The first cone-beam inversion formula for real-valued functions is given by Tuy in 1983; this formula was a Fourier-based method (Heang K. Tuy "An Inversion Formula for Cone-Beam Reconstruction," *SIAM J. Appl. Math*, Vol. 43, 1983, pp. 546–552). Smith's paper in 1985 established connections between the cone-beam data and the second-order radial derivative of the Radon transform, $R''f$ (Bruce D. Smith "Image Reconstruction from Cone-Beam Projections: Necessary and Sufficient Conditions and Reconstruction Methods," *IEEE Trans. Med. Imag.*, Vol. 4, 1985, pp. 14–25). The most important contribution in these early derivations is a clear understanding of the data sufficiency condition for an exact reconstruction, that is, almost all planes passing by the support of the object shall intersect with the source orbit. A source orbit that satisfies this condition is called a complete source orbit or a complete scan path.

The next significant breakthrough came with the discovery of the Fundamental Relation by Grangeat (Pierre Grangeat "Mathematical Framework of Cone-Beam 3D Reconstruction via the First Derivative of the Radon Transform," *Mathematical methods in tomography, Lecture notes in mathematics* 1497, 1991, pp. 66–97. The Fundamental Relation relates the cone-beam data on a slice of fan beams inside each cone-beam projection to the first-order radial derivative of the Radon transform, $R'f$. $R'f$ serves as an implicit link between the cone-beam data and $R''f$, the second-order radial derivative of the Radon transform. $R''f$ is needed in order to use Eqn. (3); $R''f$ is then backprojected to recover $f$.

Though substantial progress has been made during the last two decades, the solutions for exact cone-beam reconstruction are still not fully satisfying. In many of the reconstruction methods that have been developed, the backprojection-differentiation operation inherited from the Radon formula appears ad hoc and is the most time-consuming step in the reconstruction.

The well-known filtered backprojection (FBP) cone-beam reconstruction technique, which is widely used in industry, is given by Feldkamp (FDK) et al. for circular source orbits (L. A. Feldkamp, L. C. David and J. W. Kress "Practical Cone-Beam Algorithm," *J. Opt. Soc. Am. A.*, Vol. 1, No. 6, 1984, pp. 612–619). In such a case, data from cone-beams with narrow angles is treated in an approximate way using extensions of two-dimensional fan-beam methods. FDK's reconstruction procedure is easy to implement; however, it only provides reasonably good reconstruction near the midplane and cannot be used for wide cone angles. Hence, alternative reconstruction methods and the embodying imaging apparatus are still being sought, particularly for the cone-beam systems equipped with a large area detector.

In designing a dedicated cone-beam imaging system, finding a proper source orbit is a challenge. The selection of a good source orbit not only depends on the dimension of the object being scanned, but also depends on the geometric measurements such as the allowed source-to-object and detector-to-object separation. An important condition for accurate reconstruction is the data sufficiency condition. Another desirable feature is the symmetry. The Radon space can be more evenly sampled if the source orbit exhibits a similar symmetric property as the object being scanned.

Among various source orbits that have been proposed, sinusoidal trajectory and helical trajectory meet both conditions. Though advantageous in their sampling performance, reconstruction procedures using these two scan paths have yet to achieve the desired efficiency. The principal difficulty encountered in the reconstruction is caused by the sophisticated mapping from the local projection geometry to the Radon space geometry characteristic to many non-planar source orbits.

Other approaches use two orthogonal planar trajectories such as circle-plus-circle, circle-plus-line and circle-plus-arc to fulfill the data sufficiency condition. Although the hybrid methods combine cone-beam data from two simpler scanning processes, they have two major disadvantages. First, the discontinuity in the mechanical movement makes them less attractive in practice. Second, sampling in the Radon space where the backprojection takes place is not balanced under these hybrid scanning geometries; this limits the reconstruction accuracy.

SUMMARY

Apparatus and methods for three-dimensional cone-beam imaging are disclosed herein. The methods and apparatus involve use of a radiation source for generating a cone beam of radiation, an object to be scanned, and a detector.

The radiation source is initially positioned on a predetermined scan path, particularly a biquadratic curve or helix. The source generates projection of cone-beam radiation from a common focal point. The projection, which comprises a plurality of projection "rays", passes from the source through the object, and the object attenuates the cone-beam projection as it passes therethrough. The radiation intensity of the attenuated cone-beam image is then detected on an area detector positioned on an opposite side of the object from the detector, and a two-dimensional attenuation image of the cone-beam projection is obtained from the detected radiation intensities.

The methods include a novel paradigm for reconstructing a three-dimensional image from the cone-beam projections, wherein a new technique, referred to as moving frame reconstruction (MFR), is introduced. MFR has the ability to invert a set of cone-beam images progressively and simultaneously in conjunction with the X-ray scanning process. It allows exact cone-beam reconstruction for universal source orbit that satisfies the data sufficiency condition. The advantage is that a source orbit optimal for a given object can be used in scanning, resulting in a more accurate reconstruction and enhanced isotropic resolution.

In terms of the reconstruction procedure, the most complex and expensive computation in cone-beam imaging lies in the backprojection-differentiation operation. Described herein is a technique that enables systematic implementation of the backprojection-differentiation operation and which can be described by the following procedures.

After the two-dimensional attenuation image is obtained, an intermediate transform function, namely, the first-order radial derivative of the Radon transform, is obtained on a set of planes passing through the focal point. The source is then repositioned and the steps are repeated; i.e., a cone-beam is passed through the object from the new position and detected by the detector, and the detector generates another attenuation image, which is used to obtain another intermediate transform function.

After two or more repetitions of the above steps, the intermediate transform functions acquired from consecutive attenuation images are filtered using a moving-frame technique to obtain the second-order radial derivative of the Radon transform. The second-order radial derivative of the Radon transform is then backprojected in the three-dimensional space along each projection ray to generate an intermediate, locally reconstructed, three-dimensional image with constant values assigned along each projection ray. The procedure comprising repositioning the source; obtaining (a) a two-dimensional attenuation image, (b) an intermediate transform function, and (c) a second-order radial derivative of the Radon transform; and then backprojecting that second-order radial derivative of the Radon transform is then repeated at least once.

Finally, the plurality of intermediate, locally reconstructed, three-dimensional images are summed to obtain an ultimate, reconstructed, three-dimensional image of the object.

In one embodiment, the method for performing the above-described steps of backprojecting the second-order radial derivative and summing the plurality of intermediate, locally reconstructed, three-dimensional images can be expressed as the following decomposed Radon formula:

$$f(x) = -\frac{1}{8\pi^2} \int_A \left\{ \int_{\beta \in [x - \Phi(\lambda)]^\perp, \beta \in S^2} R'' f(\Phi(\lambda) \cdot \beta, \beta) \frac{|\Phi'(\lambda) \cdot \beta|}{M(\lambda, \beta)} d\beta \right\} d\lambda, \quad (4)$$

where $\Phi(\lambda)$, the parameterized source orbit, is a complete path and is almost everywhere analytic, which means infinitely differentiable everywhere except a zero measure set. $M(\lambda, \beta)$ is the number of times that a plane passing by $\Phi(\lambda)$ and having unit normal $\beta$ intersects with the source orbit. The described plane can be written as $L_{l,\beta}$, where $l = \Phi(\lambda) \cdot \beta$. Hence the function $M(\lambda, \beta)$ is also considered as a function of $l$ and $\beta$; without confusion, we can write it as $M(l, \beta)$, and it is referred to as the redundancy function or multiplicity function.

The above mathematical formulism serves two prevailing geometric constraints underlying most of the cone-beam tomographic systems.

First, within each cone-beam projection, all the planes passing through a particular projection line have normal perpendicular to the same projection ray. As a result, back-projection orientation can be constrained onto a unit circle. This reduction of the backprojection from three-dimensional space to two-dimensional space brings great efficiency to the reconstruction method.

Second, as a radiation source traverses along the source orbit, each backprojection orientation undergoes a rigid rotation that can be described by a moving basis (e.g., determined by the local properties of the source orbit). The moving basis serves as a coordinate transform from the local coordinates in each projection frame to the global coordinates in the Radon space. As long as the source orbit satisfies the data sufficiency condition, one can succeed in decomposing the three-dimensional backprojection into a series of two-dimensional backprojections in accordance with the scanning geometry.

The source trajectory can be stored as software code in a computer-readable medium coupled with a computer processor. The processor, in turn is coupled with mechanical apparatus for moving the source along the source trajectory, and the processor following the instructions of the code so directs the source along the source trajectory and also directs the detector along a corollary trajectory. Alternatively, the code directs the rotation of the object to generate a similar relative displacement to the source and detector. Intensity values from the detector are communicated to computer-readable memory, where they are stored in digital form. Additional software code processes the intensity values in accordance with the reconstruction method described above to obtain the ultimate, reconstructed, three-dimensional image of the object.

Source orbits disclosed herein are aimed at offering better sampling performance in the Radon space and consequently better image qualities in the reconstruction. A new family of source orbits disclosed herein is the biquardatic source curve. The parameters of the biquadratic source curve can be tuned in accordance with the dimension of the scanned object. Another benefit of using the biquadratic curve is that it has at most four intersections with a plane in the three-dimensional space. We are able to give an analytic procedure for deciding the number of intersections between a specified source orbit and an arbitrary plane in the three-dimensional space; accurate determination of the multiplicity function is important for cone-beam reconstruction because it determines the weights of each plane passing by a particular source point along the source orbit.

The disclosed technique allows simple and systematic approach to cone-beam tomographic reconstructions in general. A number of different source-detector configurations and orientations, as well as a large family of scanning orbits satisfying the so-called data sufficiency condition can be successfully treated in a unified reconstruction framework with greater ease, simplicity and improved efficiency. For example, methods involving helical source orbits are described herein, and adaptations made to treat the truncated helical cone-beam reconstruction are also described.

Figure 1:
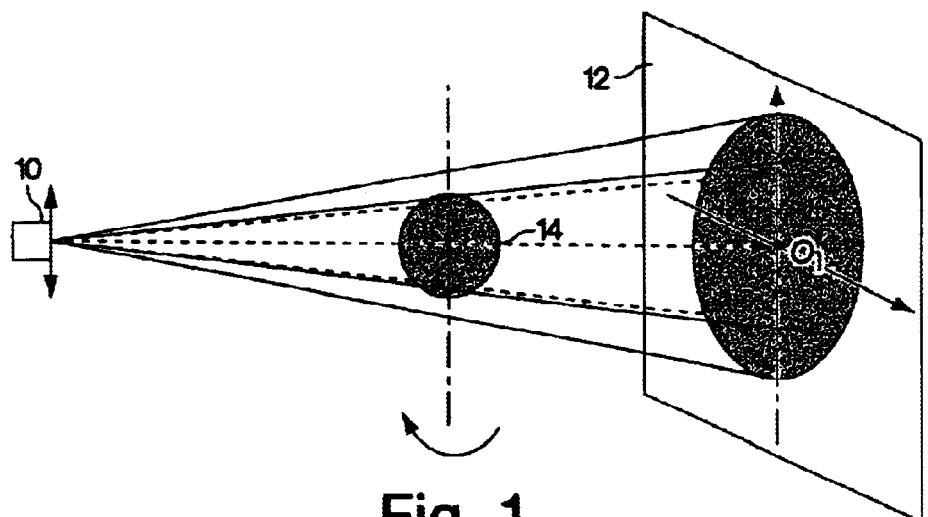
FIG. 1 provides a schematic illustration of a cone-beam imaging apparatus.

The foregoing will be more apparent from the following, more-particular description. In the drawings, like reference characters refer to the same or similar parts throughout the different views. The drawings are not necessarily to scale, emphasis instead being placed upon illustrating particular principles, discussed below.

DETAILED DESCRIPTION

Figure 2:
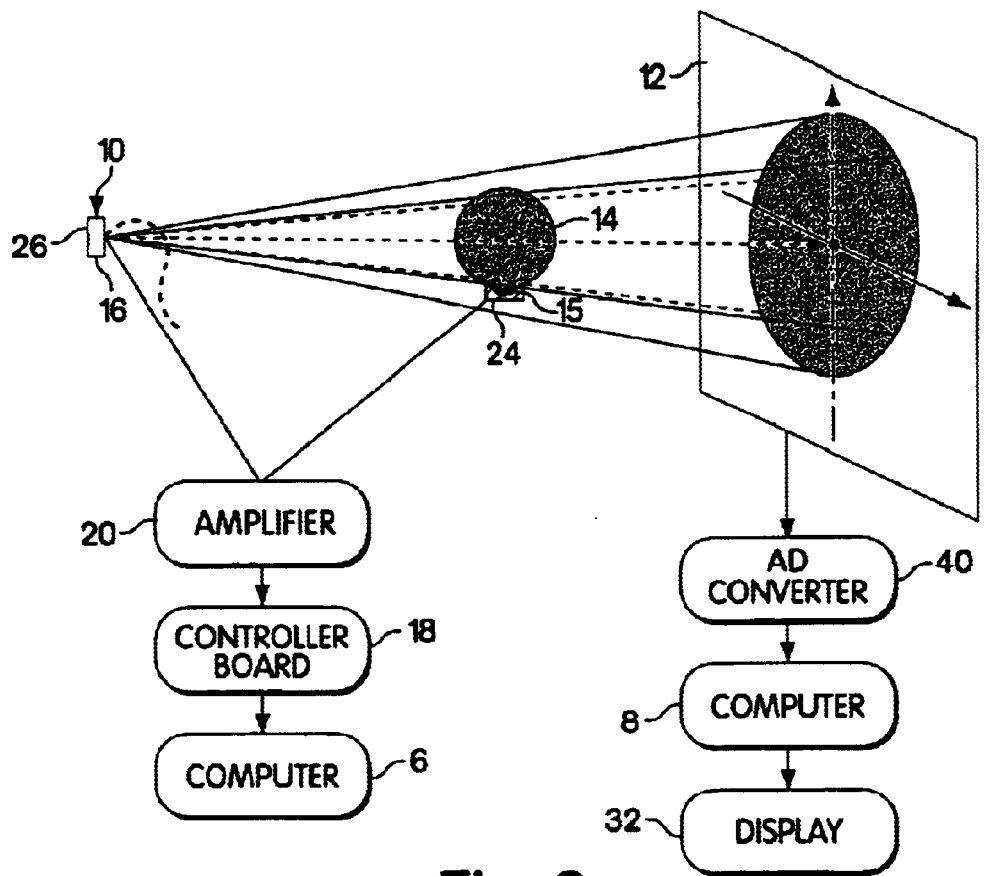
FIG. 2 illustrates a typical cone-beam imaging system with a radiation source and a two-dimensional area detector rotating around the object being scanned.

FIG. 2 illustrates a suitable apparatus for generating and detecting a plurality of cone-beam projections from a radiation source as well as recovering the three-dimensional attenuation map inside the object being scanned from the collected cone-beam projection measurement. Specifically, the physical hardware of a cone-beam imaging system comprises a radiation source 10, a two-dimensional area detector 12 that receives the attenuated rays emitting from the point source and passing by the object 14, at least two motors 15 and 16 (the source and detector can be controlled by a single motor or separately by two different motors), which are accountable for the relative movement between the source-detector system and the object 14, an analog-to-digital converter 40 that converts the cone-beam signals detected by the area detector into a digital format that enters the computer system 8 as input, and the computer system 8, which stores, processes the converted cone-beam data to reconstruct the attenuation distribution inside the object. The output of the reconstruction is a three-dimensional array that can be recorded in a readable media and displayed by an imaging or graphical display engine 32.

More specifically, the radiation source could be X rays, gamma rays, electron beams and other types of probing beams that travel along straight lines. The two-dimensional detector is placed on the opposite side of the radiation source behind the scanned object. It measures the transmitted flux of radiation. The detector array is covered by multiple rows and columns of detector elements. The surface of the detector can be planar or curved. A cone-beam projection comprises a plurality of projection rays connecting the radiation source and a plurality of detector elements on the detector surface. Beam collimation to form conical projections can be done either by choosing a radiation source with a cone-beam collimator, or by tiling collimators on the top of the detector surface so that the rays received by the detector elements on the detector converge to the same focal point at the source. The relative position of the source and detector are fixed during the scanning process, whereas, the relative position of the source-detector pair and the object is controlled by the motors attached to the object support 25 and the source-detector support 26 (or separately to the source and detector). Various mechanisms for rotating the radiation source and the detector around the object are known in the art. In one embodiment, the object is secured on a rotational turntable driven by a motor while the source and detector are mounted on an independent mechanical support such as a pair of parallel slides whose synchronized translation is under the control of another motor. In another embodiment, like in the medical CT scan, the radiation source and the detector are mounted on a cylindrical gantry that rotates, and the object undergoes a simultaneous translation in the direction orthogonal to the rotational gantry. In both cases, the radiation source and the detector seem to travel along a smooth space curve while remaining at a fixed position relative to one another. This curve followed by the radiation source relative to the scanned object is the source orbit or the scan path.

Furthermore, computer 6 stores code to implement the prescribed scan path through discrete steps of rotation and translation. The motors are driven by a controller board 18 which is capable of receiving the signals from computer 6 and generating the commands that set the motors into a synchronized movement. The output of the controller is amplified by the amplifier 20 so that the motors get the required power for the motion.

The imaging display engine 32 is capable of displaying two-dimensional images of the reconstructed attenuation map on an arbitrary cross-section, or processing the reconstructed three-dimensional array using a rendering algorithm to produce a three-dimensional anatomical representation of the object that can be viewed from various angles on a computer screen.

There is another type of system assembly, referred to as a C-arm system, that is capable of generating and detecting a plurality of cone-beam projections from a radiation source as well as recovering the three-dimensional attenuation map inside the object being scanned from the collected cone-beam projection measurement. In a C-arm system (FIG. 3), the object of interest 14, such as a patient, is placed on a support 101. Radiation source 10 and area detector 12 can be anchored on two slides 104 and 106 that extend out from the two ends of a rigid arm 100. The two slides 104 and 106 can have flat or curved surfaces. The rigid arm 100 has a wide opening like a letter C and is connected to a base 102 fixed on a floor, or a wall, or a ceiling. The connectors 111 and 113 attaching the source and detector to the two slides 104 and 106 are flexible enough so that the source 10 and detector 12 can be oriented in arbitrary directions. The object 14 is seated in between the source 10 and the detector 12 during the data acquisition.

Figure 3:
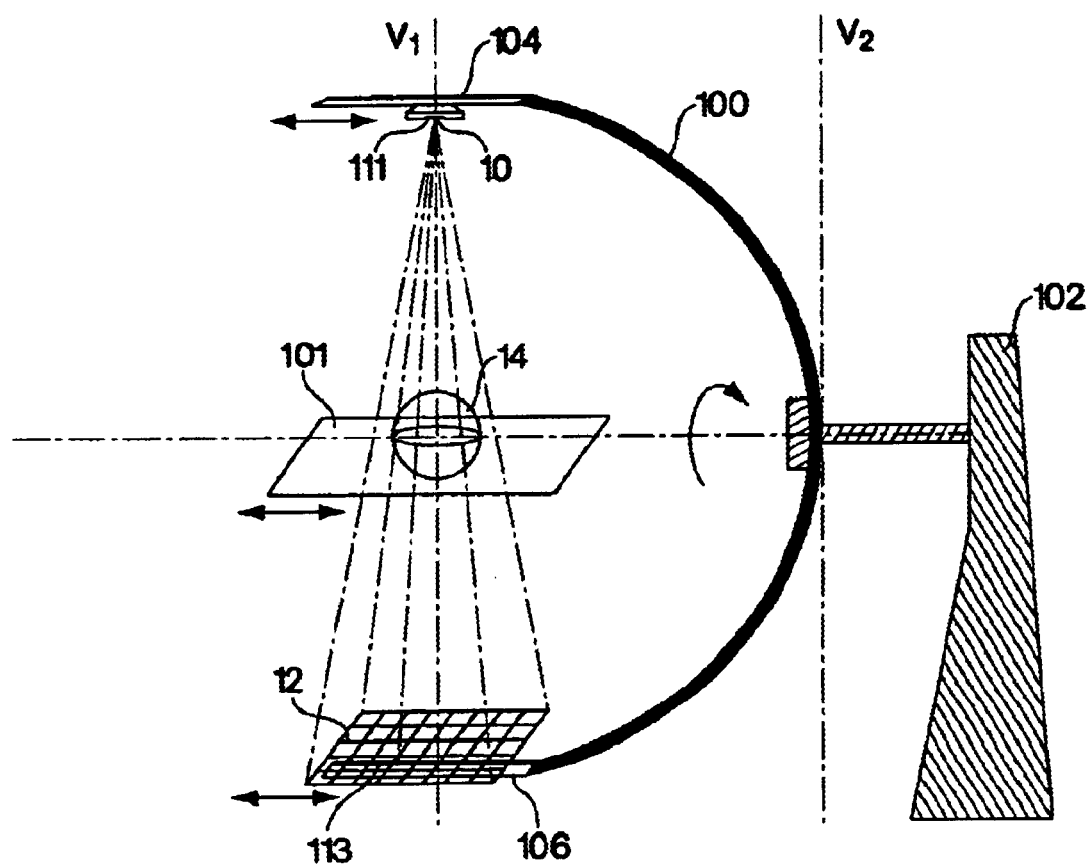
FIG. 3 provides a schematic illustration of a C-arm cone-beam imaging system with a radiation source and a two-dimensional area detector rotating around the object being scanned.

A rotary motor propels the rigid arm 100 to rotate around the horizontal axis passing through the object 14; this axis of rotation is called the axial axis. The two slides 104 and 106 extending from the two ends of the arm and coupled with two linear motors, allow the source and the detector to move in the axial direction independently. When simultaneous sliding and rotation are performed, the radiation source follows a nonplanar scan path relative to the examined object. Alternatively, instead of using the two linear slides 104 and 106, either the object support 101 or the rigid arm 100 has a sliding mechanism and is able to move along the axial direction. Furthermore, if the object support 101 is allowed to rotate around a vertical axis, $V_1$, passing through the center of the support 102, as shown in FIG. 3, or if the rigid arm 100 is capable of rotating around the vertical axis $V_2$, passing through the connector of the rigid arm with its base), more degrees of freedom can be introduced thus more scan paths can be generated. Compared to the cone-beam imaging apparatus earlier discussed, the C-arm is an open system. It is more flexible in terms of generating an arbitrary scan path, which also requires sophisticated coordinate calibration and determination. However, the data acquisition geometry relative to the scanned object and the corresponding reconstruction procedure do not depart in principle from the previous system. We will use the previously described cone-beam system to illustrate our general approach.

Configuring the Source Orbit

A basic setup for a cone-beam CT scan is to establish the source orbit. Assume that the source orbit is parameterized by $\Phi(\lambda)=(\phi_1(\lambda), \phi_2(\lambda), \phi_3(\lambda))$, with $\lambda \in \Lambda$ being the parameter. Also assume that the source orbit resides outside the convex support of the object, denoted by $\Omega$. Data sufficiency condition requires that all or almost all planes passing by the object intersect with $\Phi(\lambda)$.

A preferred source orbit not only would satisfy the data sufficiency condition, but also would produce considerably even-sampled Radon space, which is defined as the space of all the planes passing by the object. The data sufficiency condition is imposed to ensure that the collected cone-beam data, after an integral transform, would fill the entire transform space so that backprojection could be carried out without missing data. A uniformly sampled Radon space would lead to isotropic imaging resolution which is the ultimate, superior goal of cone-beam imaging yet to be accomplished. Uniform sampling in the Radon space means to produce a relatively even-sampled backprojection sphere everywhere in the object space—this problem does not have an exact solution but only approximate or suboptimal solutions. The size and the shape of the examined object are important factors in selecting the source orbit; e.g., the source orbits that result in good sampling performance for round and elongated objects should be different because they exhibit different kind of symmetries. Use of a source orbit that has symmetry characteristics resembling those of the object could yield a better, more isotropic imaging performance. Additionally, the separation distance between the X-ray spot and the area detector as well as the size of the detector are also important constraints to be considered and accordingly to be compromised when choosing a suitable source orbit.

We propose a new family of source orbits called biquadratic curves. Biquadratic curves are the intersection of two quadratic surfaces such as cylinder, paraboloid, hyperboloid and ellipsoid. They have nice symmetry property and their shape and elongation can be altered by adjusting a few parameters. In addition, selecting a source orbit from the biquadratic family is advantageous in that the number of the intersections of an arbitrary plane with the source orbit can be evaluated analytically. The number of intersections of a plane with the source orbit defines the multiplicity function. Accurate determination of this multiplicity function is important for accurate cone-beam image reconstruction because it determines the weight of a particular plane within each cone-beam projection in a local reconstruction. With the biquadratic curve, the multiplicity function can be calculated on the flight with an explicit, analytical approach, whereas, for most nonplanar curves, one can only resort to ad-hoc numerical method for solving nonlinear equations which are difficult to be implemented online.

The implicit equations for the cylinder, paraboloid, hyperboloid and ellipsoid are:

Cylinder: $x^2+y^2=R^2$ (9)

Hyperboloid: $z^2=a^2x^2+b^2y^2+c$ (10)

Paraboloid: $z=a^2x^2+b^2y^2+c$ (11)

Ellipsoid: $z^2=-a^2x^2-b^2y^2+c$. (12)

Figure 4:
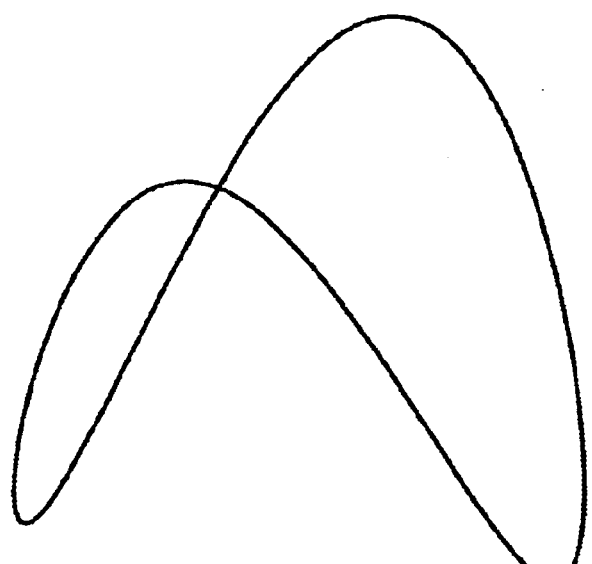
FIG. 4 illustrates a biquadratic source orbit which is the intersection curve of a cylinder and a hyperboloid.
Figure 5:
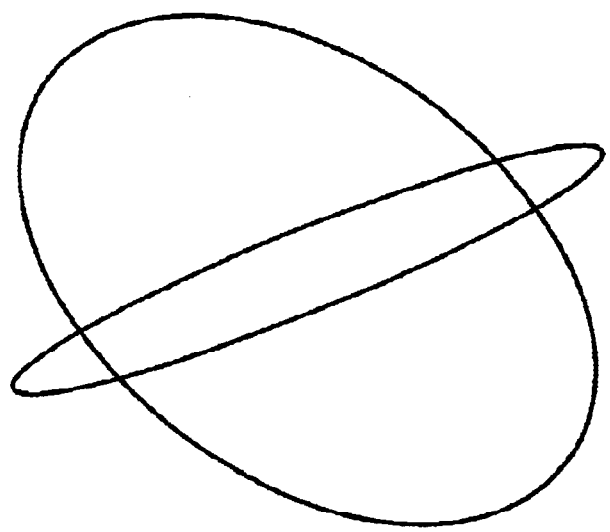
FIG. 5 illustrates a biquadratic source orbit intersected by a cylinder and the ellipsoid.

Any two of the above quadratic surfaces intersects at a biquadratic curve (FIGS. 4–5). Note that only the upper half of the hyperboloid surface ($z\geq 0$) will be considered.

When the source remains at a constant distance away from the rotational axis, the source orbit is confined on a cylinder. Let the rotational axis pass through the center of the object as shown in FIG. 1 a vertical line. A biquadratic curve can be generated by intersecting the cylinder with another quadratic surface chosen from Eqn. (10), (11) and (12). For illustration, we select the hyperboloid Eqn. (10).

To find the number of the intersections of an arbitrary plane $L_{l,\beta}$ with the intersection curve generated by Eqn. (9) and Eqn. (10), we write the plane equation as $\beta_1 x+\beta_2 y+\beta_3 z=l$ (13)

where $\beta_1$, $\beta_2$ and $\beta_3$ are the three components of the unit normal vector, $\beta$, of the plane. If $\beta_3 \neq 0$, Eqn. (9) can be used to eliminate the variable y from Eqn. (10) and Eqn. (13):

$z^2=a^2x^2+b^2(R^2-x^2)+c$, $x\in[-R,R]$ (14)

$z=-\frac{\beta_1}{\beta_3}x \pm \frac{\beta_2}{\beta_3}\sqrt{R^2-x^2}+\frac{l}{\beta_3}$, $x\in[-R,R]$ (15)

Combining Eqn. (14) and (15) yields $a^2x^2+b^2(R^2-x^2)+c=\left(-\frac{\beta_1}{\beta_3}x \pm \frac{\beta_2}{\beta_3}\sqrt{R^2-x^2}+\frac{l}{\beta_3}\right)^2$, (16)

$x\in[-R,R]$

Eqn. (16) can be rearranged into a quartic equation (fourth-degree polynomial equation), for which, analytical solutions are known in the art and can be readily obtained using, e.g., the commercially available software program, MATHEMATICA, from Wolfram Research (Champaign, Ill., USA). Since the solutions are given explicitly, we can check if each real root is within [−R, R]. If it is, then this root corresponds to an intersection point. The number of intersections of a plane with a biquadratic curve is either 0, 1, 2, 3, or 4. Equation 16 can be incorporated into software to find the number of intersections using the analytical formula for the roots of the quartic equation. Similar results can be obtained for $\beta_3=0$.

The parametric representation of the biquadratic source orbit generated by Eqn. (9) and Eqn. (10) can be written as $\phi_1(\lambda)=R\cos\lambda$, $\phi_2(\lambda)=R\sin\lambda$, with $\lambda\in[0, 2\pi]$ and R the distance between the source and the rotational axis (this distance is fixed), and the linear translation of the source orbit in the z-dimension is given by $\phi_3(\lambda)=\sqrt{a^2R^2\cos^2\lambda+b^2R^2\sin^2\lambda+c}$. (17)

Figure 6:
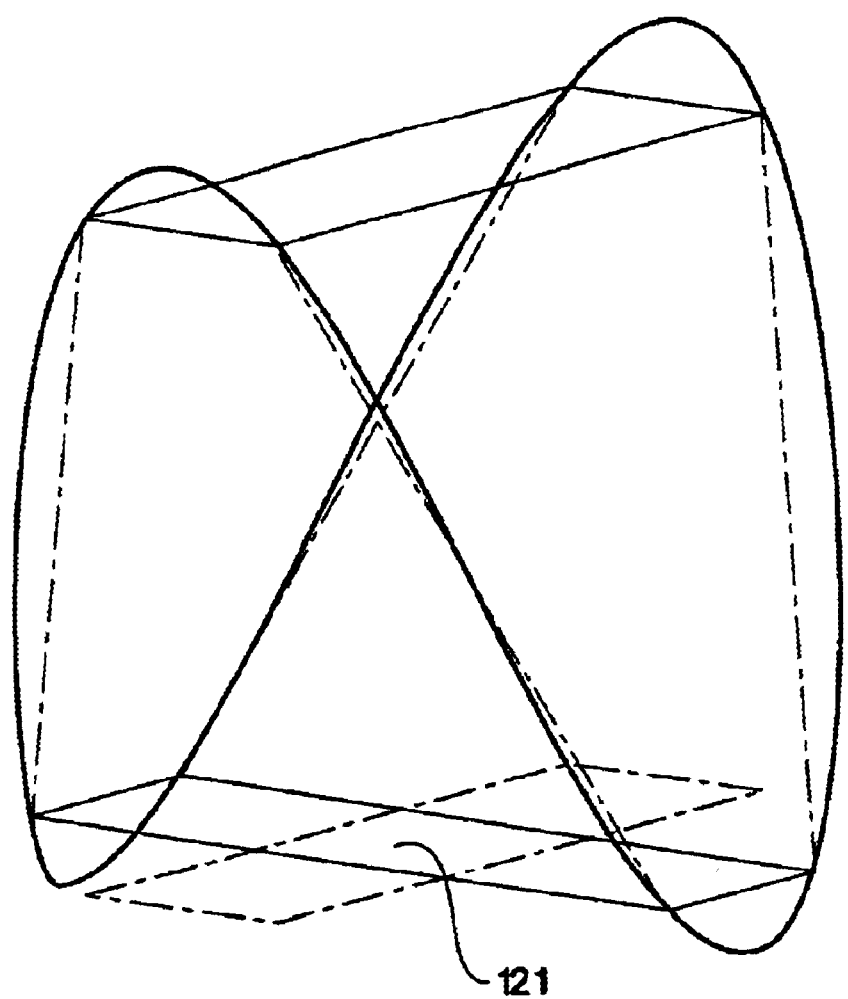
FIG. 6 provides a visualization of two horizontal cutting planes intersecting with the biquadratic source orbit and the polyhedron formed by the eight intersections.

The biquadratic curve thus generated is highly symmetric. In addition, its shape can be adjusted by the parameters R, a and b in accordance with the dimension of the object so that the data sufficiency condition can be met. Note that a and b affect the amplitude of the curve; the ratio of curve's amplitude and R affect the elongation of the curve. Assume that the object has a square base with width w and height h. In order for every plane passing through the object intersects with the source orbit, the object needs to be inside the convex hull of the source orbit. Let two horizontal cutting planes intersect with the source orbit near the top and bottom of the curve. In addition, assume that the two parallel planes are equally distant from the maximum point and the minimum point of the source curve respectively. The eight intersections of the two planes with the biquadratic curve form a trapezoid as shown in FIG. 6. If the object is completely inside the trapezoid, the object is also inside the convex hull of the source orbit. This can be achieved by increasing the amplitude of the curve, i.e., increasing a (without loss of generality, we assume that a>b), or the radius of the cylinder R or both. A simple check is that the amplitude of the curve shall be greater than the height of the object, and, the base of the object, when projected onto a horizontal plane, shall be enclosed by the common area 121 projected from the top face and bottom face of the trapezoid onto the same horizontal plane (FIG. 6).

Figure 7:
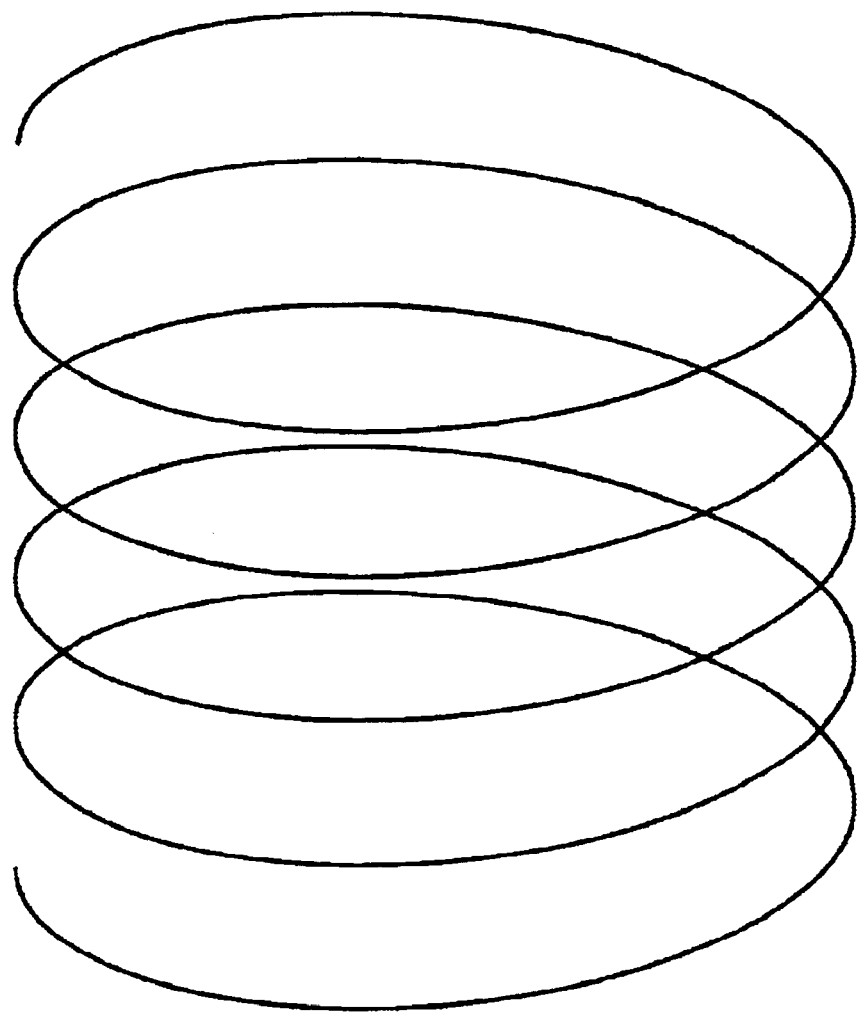
FIG. 7 illustrates a helical source orbit.

In addition to the biquadratic source orbit, one can use any scan path that is both complete and analytic (which means that the curve is infinitely differentiable almost everywhere with exception allowed for a zero measure set). Most of the curves we encounter are analytic curves. When the simultaneous rotation and translation both have constant speed, the resulting source orbit is a helix (FIG. 7) that can be parameterized by $\Phi(\lambda)=\left(R\cos\lambda, R\sin\lambda, p\frac{\lambda}{2\pi}\right)$, $\lambda\in[0, n\pi]$ where p is called the pitch of the helix. The pitch determines the elevation of the curve in one helical turn.

Cone-beam reconstruction using complete scan path allows exact reconstruction. A more general embodiment encompasses any scan path that is everywhere differentiable except at a finite number of points, such as a circular trajectory $\Phi(\lambda)=(R\cos\lambda, R\sin\lambda, 0)$, $\lambda\in[0,2\pi]$ Circular scan path is not complete (planes above or below and parallel to the circle never meet with the scan path), nevertheless, it allows approximate reconstruction using the disclosed reconstruction method.

Detector Orientation

Figure 8:
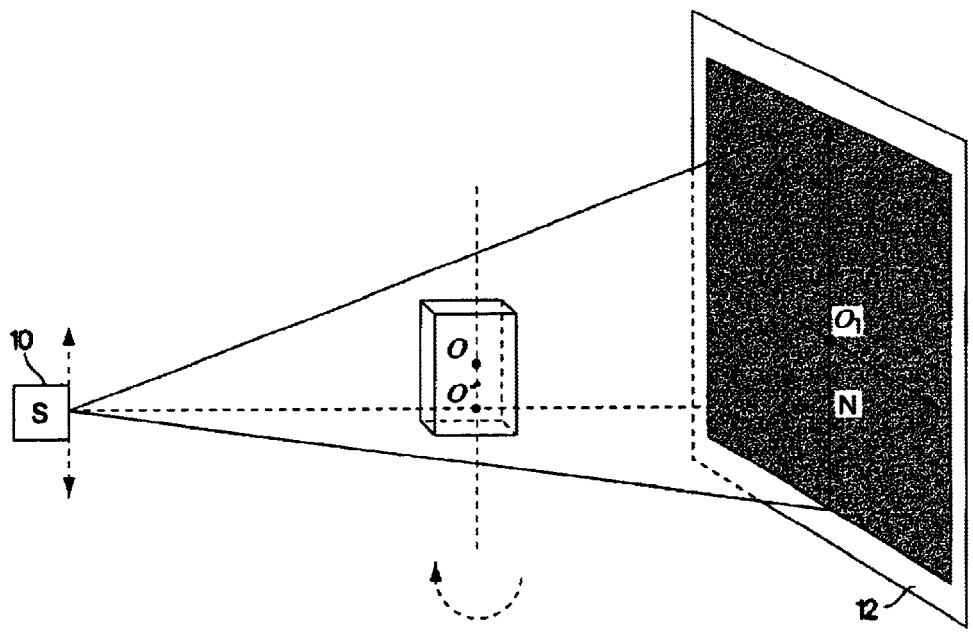
FIG. 8 is an illustration of a second exemplary detector orientation (different from the detector orientation illustrated in FIG. 1).

Other than the configuration of the X-ray source orbit, geometric arrangement of the detector is another practical concern in a cone-beam imaging system. The development in detector technology provides increasingly high resolution X-ray detectors such as the panel system. In one exemplary embodiment, a flat panel detector is used with its vertical-axis parallel to the rotational axis of the source orbit and its horizontal axis parallel to the projection of the tangent of the source orbit at the specified source position onto a horizontal plane (see FIG. 8). Denote by S the source position. Let N be the point where the perpendicular line from the source to the detector plane meets the detector. Let the distance from the detector to the rotational axis be D, which is fixed. The center of the detector image, denoted by $O_I$, may not coincide with N, especially when the detector area is to be maximally used. O' denotes the intersection of the perpendicular line SN and the rotational axis. With the described detector orientation, data acquisition geometry has a striking cylindrical symmetry. It is particularly suitable for scanning object with the same kind of cylindrical symmetry. Alternatively, if spherical symmetry is characteristic to the object being scanned, one can lay the two-dimensional detector array on a plane perpendicular to the line connecting the source and the origin at the center of the object (as shown in FIG. 1).

Figure 9:
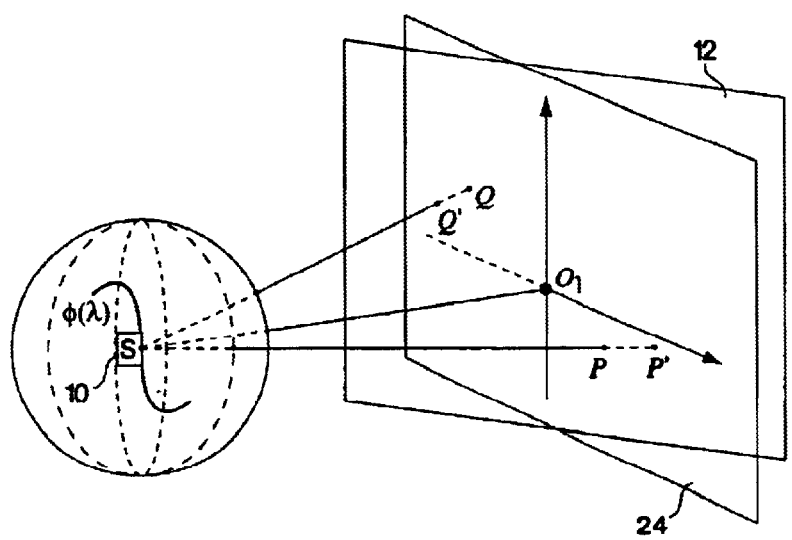
FIG. 9 illustrates the projection of rays from the radiation source onto the detector surface, where there is a one-to-one correspondence between image pixels on the standard image plane and detector elements on the detector surface.

If the two-dimensional detector surface is not planar but curved or is not oriented in the way we described, we can use one of the above two configurations that closely resembles a real configuration as the standard image plane. The pixels on any detector surface can be one-to-one mapped to a chosen standard image plane 24 by a geometric transform (see FIG. 9). Given a point on a real detector, the corresponding pixel on the standard image plane is the intersection of the standard image plane with the line connecting the source to the point on the detector.

Image Reconstruction

Assume that a function $f$ on $\mathbb{R}^3$ represents the three-dimensional radiation attenuation inside the object being scanned and $f$ has a finite support $\Omega$. The cone-beam image obtained from a particular point source $\Phi(\lambda)$ measures the half line integrals of attenuation along rays passing through $\Phi(\lambda)$:

$$g(\lambda, \alpha) = \int_0^{+\infty} f(\Phi(\lambda) + t\alpha) dt, \ \alpha \in S^2. \quad (18)$$

We name g the X-ray transform of $f$.

There are two distinguished spaces when we process the cone-beam image data. One is the object space in which the three-dimensional attenuation map of the object is to be evaluated. The other is the Radon space, or called the transform space, which is the space of all the planes in $\mathbb{R}^3$. Object space and transform space cohabit in the same physical space but they have separate coordinate systems.

Assume that the object space is a uniformly spaced lattice in Cartesian coordinate, say $\{O: x, y, z\}$ with origin, O, at the center of the object, and the z-axis is aligned with the rotational axis of the source orbit. This coordinate is called the global reference frame.

The coordinates identifying a particular Radon plane in the Radon space are $\beta$, the unit normal vector, and l, the perpendicular distance of the plane to the origin. (l, $\beta$) are the global coordinates of the Radon space. One can visualize the Radon space by attaching to each point, $x \in \mathbb{R}^3$, a two-dimensional unit sphere, and the points on $S_x^2$ represent the unit normal of all the planes through x. This is the backprojection sphere we mentioned earlier. Such a representation of the Radon space is redundant since many planes passing by the object intersect with the source orbit multiple times. In the mean time, this redundant representation is advantageous in the reconstruction context since the differential-backprojection operator in the Radon formula (Eqn. (3)), when evaluated for point x, acts on all or almost all planes passing through x but no other planes. The sphere $S_x^2$ is therefore handy for visualizing the geometric computation at the point x, where the function is to be recovered. In the ultimate reconstruction, however, the redundancy is taken into account and each Radon plane is weighted by the number of times it meets with the source orbit, which is the multiplicity function we discussed while studying the biquadratic curves.

Figure 10:
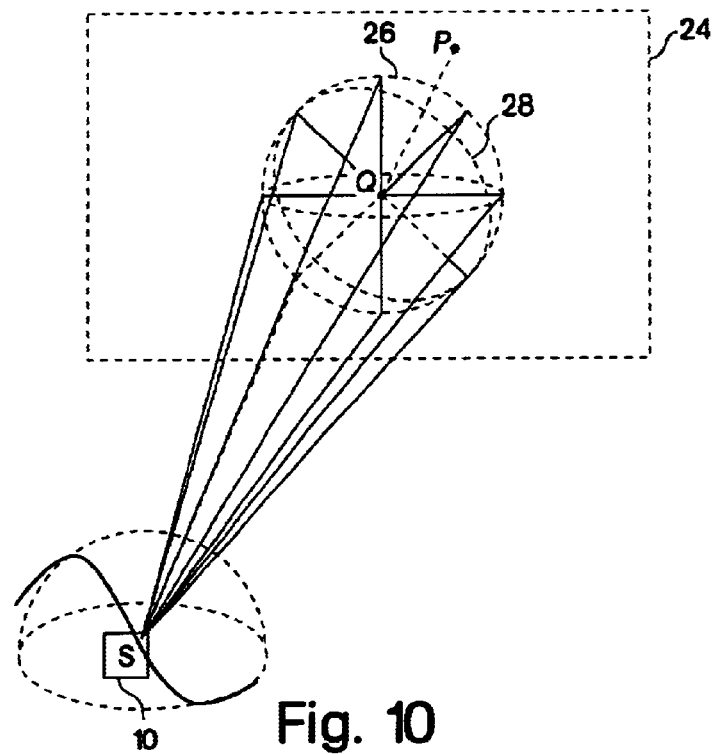
FIG. 10 illustrates a bundle of Radon planes intersecting at a projection line.

Next, a cone-beam projection from a point source is examined. The divergent beams consist of a family of fan beam slices on those planes passing by the radiation source and an arbitrary line on the two-dimensional image plane; these planes constitute only a subset of all the planes in the projective Radon space. To be able to describe the geometric constraint raised by each cone-beam projection, a point source, say S, is selected and a projection line that connects the source S to a point P on the image plane. Then, for each point Q lying on SP, the family of planes passing by both S and Q intersect at SP. As a result, the normal directions of this set of planes are perpendicular to the projection line SP and are confined to a great circle on the backprojection sphere 26 surrounding Q (see FIG. 10). We call the great circle 28 the backprojection circle.

Figure 11:
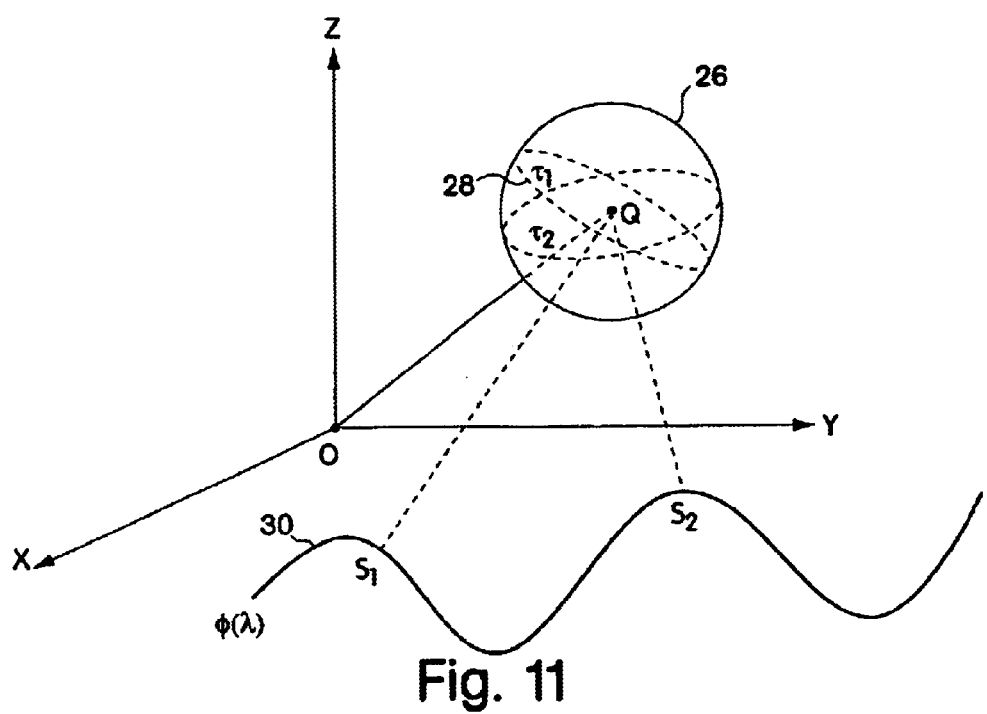
FIG. 11 illustrates the rigid rotation of the backprojection orientations from projection to projection.

As the radiation source is moved around the object, the backprojection circle rotates about Q and changes its orientation while still remaining on the backprojection sphere (see FIG. 11). It is the result of a rigid rotation. As long as the source orbit 30 satisfies the data sufficiency condition, the backprojection circles will sweep out and cover the entire backprojection sphere 26. This geometric analysis leads to the following decomposed Radon inversion formula suitable for three-dimensional cone-beam image reconstruction:

$$f(x) = -\frac{1}{8\pi^2} \int_A \left\{ \int_{\beta \in \{x-\Phi(\lambda)\}^\perp, \beta \in S^2} R''f(\Phi(\lambda) \cdot \beta, \beta) \frac{|\Phi'(\lambda) \cdot \beta|}{M(\lambda, \beta)} d\beta \right\} d\lambda, \quad (19)$$

where $\{x-\Phi(\lambda)\}^\perp$ denotes the plane perpendicular to $x-\Phi(\lambda)$ and through the origin. The derivative in $R''f$ acts on its first variable, and $M(\lambda, \beta)$ is the multiplicity function depicting the number of times that the plane $L_{\Phi(\lambda) \cdot \beta, \beta}$ intersecting with the source orbit.

Reading from Eqn. (19), there is, at each fixed source position, only one two-dimensional backprojection needs to be performed along each projection ray. The resulting value is constantly assigned to all the points lying on that ray. In order to perform this geometric computation, we need to find the coordinates for all the planes through the source point of each projection.

In each local projection frame, we are dealing only with lines (on the image plane) instead of planes. Each line, say $P_1 P_2$ (FIG. 14), on the image plane is associated to a plane that passes through the source point and intersects the plane by $P_1 P_2$. Therefore, the local coordinates of line $P_1 P_2$ on the image plane shall be transformed from and to the coordinates of the plane passing through both $P_1 P_2$ and the source point.

Figure 12:
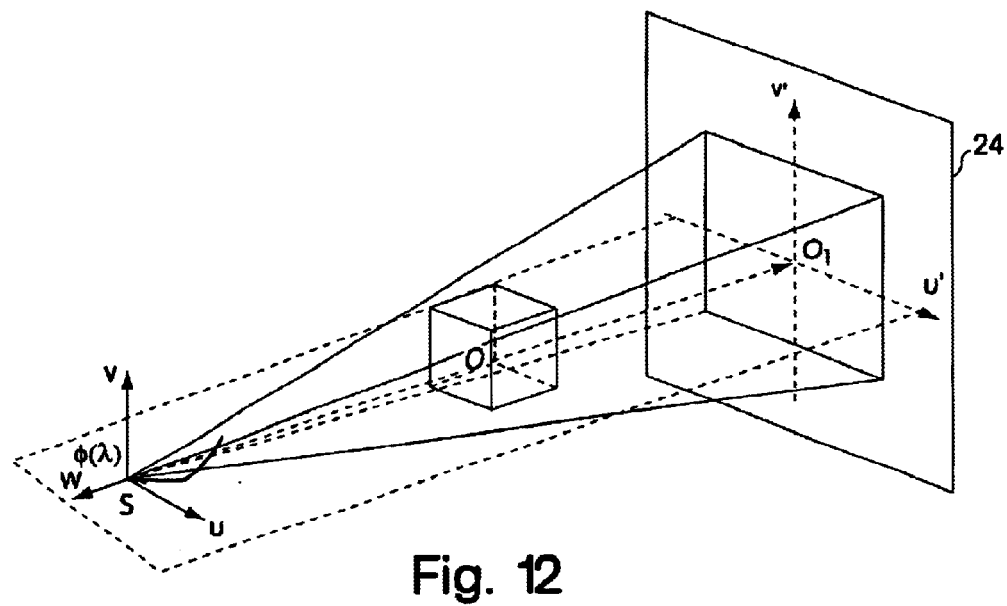
FIG. 12 provides a conceptual image of the moving basis of a first exemplary embodiment of detector orientation.

For each cone-beam projection, it is convenient to set up a local coordinate with the origin at the source. In the first exemplary embodiment of the detector orientation, we construct an orthonormal basis with one of the coordinate axes aligned with the rotational axis (the same as the z-axis in the global reference frame); and the other two axes synchronizing with the rotation of the source-detector pair relative to the object when being viewed on a horizontal plane (see FIG. 12):

$$\begin{cases} u = \dfrac{1}{\sqrt{\phi_1^2(\lambda)+\phi_2^2(\lambda)}}(-\phi_2(\lambda),\phi_1(\lambda),0) \\ v = (0,0,1) \\ w = \dfrac{1}{\sqrt{\phi_1^2(\lambda)+\phi_2^2(\lambda)}}(\phi_1(\lambda),\phi_2(\lambda),0). \end{cases} \quad (20)$$

As $\lambda$ ranges in $\Lambda$, such a construction generates a set of 3-by-3 orthonormal matrices $O(\lambda)=(u(\lambda), v(\lambda), w(\lambda))$, which are associated with a set of consecutive rotations. The sequence of orthonormal local bases is called a moving frame basis or simply moving basis with the origin anchored on the source orbit.

The way to construct a moving basis is fairly general and flexible; there are variable choices. Preferably, the moving basis should simplify the coordinate expression of the pixels on each cone-beam image plane.

Figure 13:
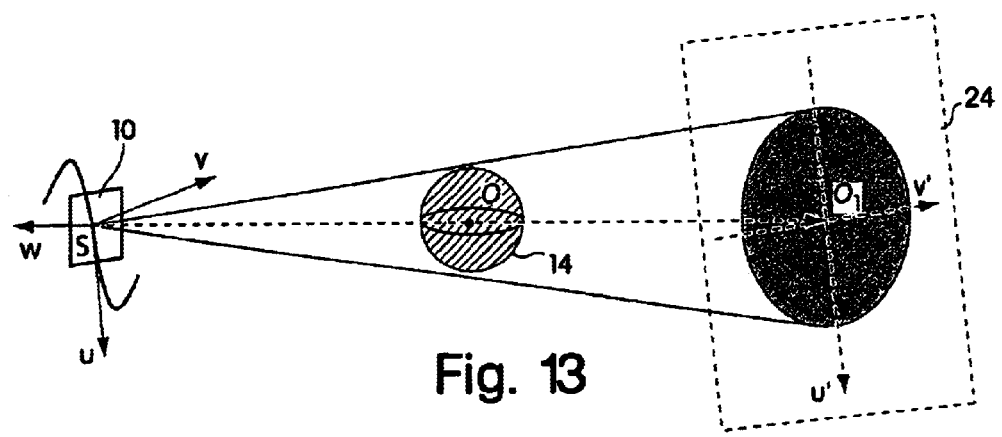
FIG. 13 provides a conceptual image of the moving basis for a second exemplary embodiment of detector orientation.

For the second exemplary embodiment of the detector orientation, we can construct the following orthonormal moving basis $$\begin{cases} w = \dfrac{\Phi(\lambda)}{|\Phi(\lambda)|} \\ v = \dfrac{w \times \Phi'(\lambda)}{|w \times \Phi'|} \\ u = v \times w, \end{cases} \quad (21)$$

with origin attached to the source orbit (see FIG. 13).

The construction of the moving basis is performed to take into account the detector orientation. In both Eqn. (20) and Eqn. (21), the local axes, u and v, are parallel with the axes on the image planes, denoted by u' and v'.

Back to Eqn. (19), the reconstruction of a three-dimensional function requires the second-order radial derivative of the Radon transform, $R''f$. This is not directly available from the X-ray transform of divergent beams. The evaluation of $R''f$ is carried out in two steps. First, one obtains the first-order radial derivative of the Radon transform within the projection; second, one calculates the second-order radial derivative of the Radon transform over the parallel planes across the projections.

Figure 14:
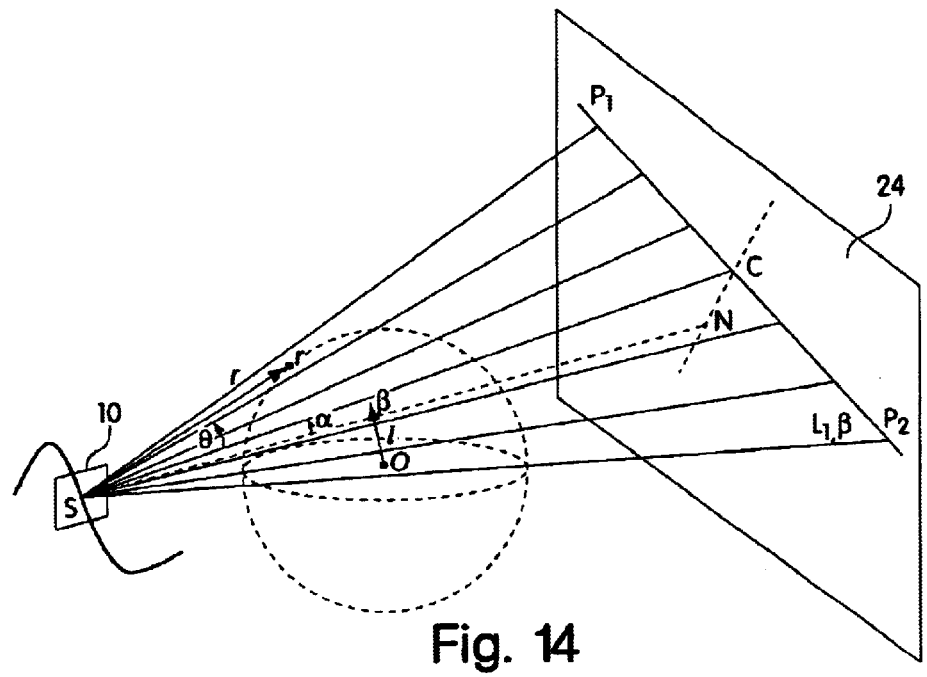
FIG. 14 provides a conceptual image of a Radon plane intersecting the image plane.

According to Grangeat's Fundamental Relation, the first-order radial derivative of the Radon transform can be obtained from the cone-beam projection data. FIG. 14 illustrates a Radon plane $L_{1,\beta}$ intersecting the support of $f$. $P_1P_2$ is the intersection line between $L_{1,\beta}$ and the image plane. Let P be an arbitrary point on $P_1P_2$. Let $\alpha$ be the angle between $L_{1,\beta}$ and the perpendicular line from the source to the image plane, SN. Angle $\alpha$ is a variable used in the local cone-beam projection frame and it serves as an intuitive link between the coordinates of planes in the local frame and the coordinates in the global Radon space. Regardless what $\beta$ is, $l=R \tan \alpha$ always holds. In other words, $\alpha$ depends only on variable l and is independent from $\beta$.

Then let the central ray be the shortest line on $L_{1,\beta}$ from the source S to the intersection line $P_1P_2$, denoted by SC. It is easy to verify that SC is perpendicular to $P_1P_2$. Because the fan beams restricted on the plane $L_{1,\beta}$ all meet at the source, it is natural to use polar coordinates on this plane, with the origin placed at the X-ray source and the axis aligned with the central ray. Denote by r and $\theta$ the radial and angular parameters respectively of the polar coordinates. We reformulate the Fundamental Relation as follows:

$$\dfrac{\partial Rf(l,\beta)}{\partial l} = -\dfrac{\partial}{\partial \alpha}\left\{\int \dfrac{1}{\cos\theta}\int f(r)dr d\theta\right\} \quad (22)$$

where the double integral is performed on the plane $L_{1,\beta}$. Note that the inner integral in Eqn. (22), $\int f(r)\, dr$, for some fixed $\theta$, represents the X-ray transform in polar coordinates on the Radon plane $L_{1,\beta}$; this is a measurement available from the cone-beam image. The double integral is the weighted line integral of the X-ray transform; the weight is the cosine of the angle between a particular ray on the Radon plane with the central ray. Note that in this formulation, SN may not pass through the global origin hence it leads to an extended version of the Fundamental Relation.

Figure 15:
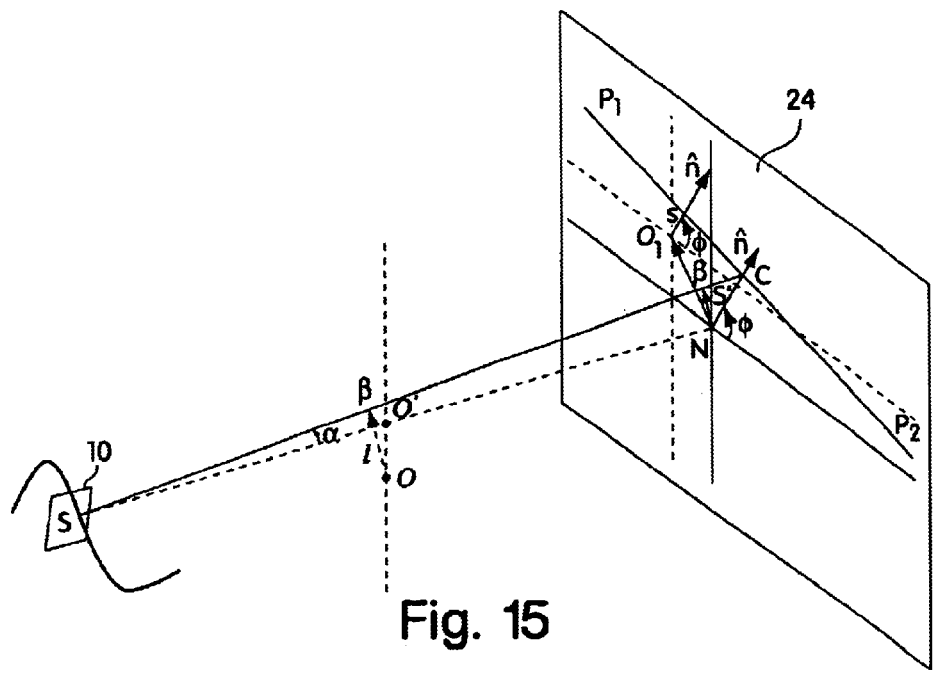
FIG. 15 illustrates how the cone-beam slice angle links the global coordinates in the Radon space and the local coordinates on the image plane.

On the image plane, assume that the radial distance of the intersection line $P_1\,P_2$ from the image center is s and its normal direction, n, form an angle $\phi$ with the u'-axis (see FIG. 15).

If the center of the image $O_1$ is aligned to the perpendicular line from the source to the image plane, SN, then $(s,\phi)$ can be expressed as $$\begin{cases} \phi = \arctan\!\left(\dfrac{\beta \cdot v}{\beta \cdot u}\right) \\ s = (R+D)\tan\alpha \end{cases} \quad (23)$$

If N is off center on the image plane, the radial distance should be offset by the projection of $NO_l$ onto the unit normal, e.g., $n=(\cos\phi, \sin\phi)$, of $P_1\,P_2$, whereas the angle $\phi$ remains the same. It yields $$\begin{cases} \phi = \arctan\!\left(\dfrac{\beta \cdot v}{\beta \cdot u}\right) \\ s = (R+D)\tan\alpha - NO_1 \cdot n \end{cases} \quad (24)$$

Eqn. (23)–(24) link the $\alpha$-coordinate to the s-coordinate in the local frame. Note that $\phi$ depends only on $\beta$, independent from $\alpha$; and, s depends solely on $\alpha$, independent from $\beta$. Therefore, the partial derivative with respect to $\alpha$ in Eqn. (17) can be evaluated through the radial derivative of the weighted line integrals on the image plane by $$\dfrac{\partial}{\partial \alpha} = \dfrac{R+D}{(1-\tan^2\alpha)}\dfrac{\partial}{\partial s}. \quad (25)$$

Figure 16:
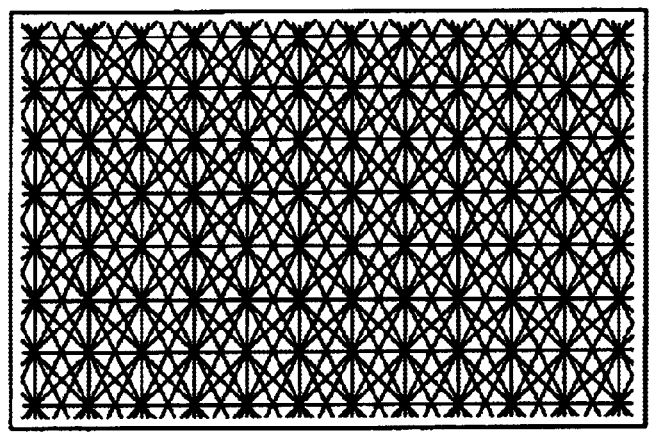
FIG. 16 provides a visualization of processed lines on the standard image plane having rational slopes.

The next step is to estimate the weighted line integrals on the image plane. However, the image plane has only discrete samples; in other words, there are no real image lines on an image plane. Nevertheless, a suitable representation of lines on a discrete grid can be determined. A line that is represented by the discrete samples on the image plane is called a virtual image line. Under symmetry consideration, we can generate a set of parallel lines with rational slopes in such a way that there are exactly the same number of lines passing through every image pixel (see FIG. 16). Note that a rational slope means it is a ratio of two integers, which allows the set of virtual lines to pass through as many grid nodes as possible.

Figure 17:
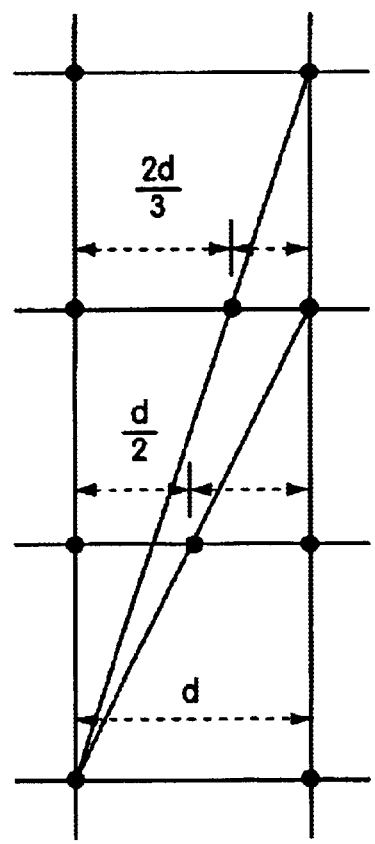
FIG. 17 illustrates an interpolation scheme for the processed lines with rational slopes.

The fact that we chose lines with rational slopes helps to align the pixels on the image plane, which offers greater computational efficiency since the weighted line integral is calculated only once for all the pixels lying on the same rational line. Besides, data interpolation can be done in a very symmetric and systematic way; data points falling between two adjacent nodes can be linearly interpolated from the values on the neighboring nodes with weights determined by the separation distance from each neighboring node (see FIG. 17).

The slopes of the finite number of rational lines can be selected in the following order as integer n increases from 0 to N:

$$\left\{\frac{n}{m}, \frac{m}{n} \mid m = \pm 1, \pm 2, \ldots N, gcf(n,m) = 1\right\}. \tag{26}$$

where gcd stands for the greatest common factor. For fixed N, the directions of those lines selected by Eqn. (26) have slightly uneven distribution on the unit circle. Note that uniform sampling in the space of lines on the image plane does not exist. Our selection of lines preserves the global symmetry while slightly compromising the local symmetry. To be more precise, we have selected the same number of lines with the same set of slopes for every image point—this contributes to a nice global symmetry, whereas, the lines passing by a particular image point are near, but not uniformly sampled.

For example, when N=3, we process the lines with slopes $$0, \infty, 1, -1, \frac{1}{2}, 2, -\frac{1}{2}, -2, \frac{1}{3}, \frac{2}{3}, 3, \frac{3}{2}, -\frac{1}{3}, -\frac{2}{3}, -3, -\frac{3}{2}.$$

For each rational line, say $P_1P_2$, on the image plane, there is a corresponding plane passing by the source and intersecting the image plane by $P_1P_2$. The global coordinates of the plane in the Radon space, $(l, \beta)$, can be calculated from $$\begin{cases} \beta = \frac{SP_1 \times SP_2}{|SP_1 \times SP_2|} \\ l = \Phi(\lambda) \cdot \beta. \end{cases} \tag{27}$$

S, $P_1$ and $P_2$ are all expressed in local coordinates. The moving basis exemplified by Eqn. (20)–(21) not only allows us to calculate the coordinate of all the planes converging at the source point inside each local projection frame, but is also a crucial technique to identify the parallel planes from two consecutive cone-beam projections which will become clear later. The local coordinates of the lines on the image plane are transformed back and forth to the global coordinates of their corresponding planes.

Hence, from the weighted line integral calculation on the image plane we obtain the first-order radial derivative of the Radon transform on a set of two-dimensional planes. The set of selected rational lines determines a set of planes whose coordinates are given by Eqn. (27).

Figure 18:
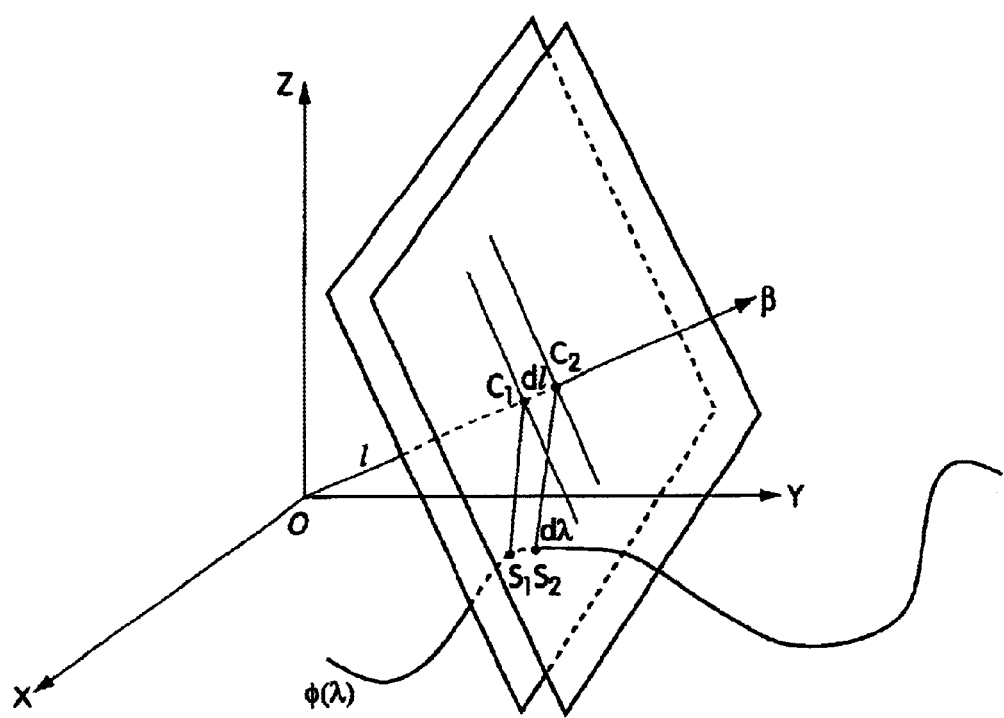
FIG. 18 provides a conceptual image of parallel planes from two consecutive projections.

To evaluate the second-order radial derivative of the Radon transform, we locate a set of planes parallel to the set of planes whose first-order radial derivative of Radon transform is available from the previous step. Since the planes passing by a single source point are non-parallel, the second-order radial derivative of the Radon transform is not available from one cone-beam projection. This second differentiation is carried out over the parallel planes from nearby projection frames. When $\beta$ is fixed (FIG. 18), the partial derivative with respect to the radial distance, l, is related to the partial derivative with respect to the source orbit parameter, $\lambda$, by $$\frac{\partial}{\partial l} = \frac{1}{\Phi'(\lambda) \cdot \beta} \frac{\partial}{\partial \lambda}. \tag{28}$$

In order to find the set of planes in the next cone-beam projection frame parallel to the set of planes selected in the current projection, the method of moving frames comes in handy. Assume $(l_1, \beta)$ is the global coordinate of a Radon plane processed by the current projection, with $l_1 = \Phi(\lambda_1) \cdot \beta$.

Figure 19:
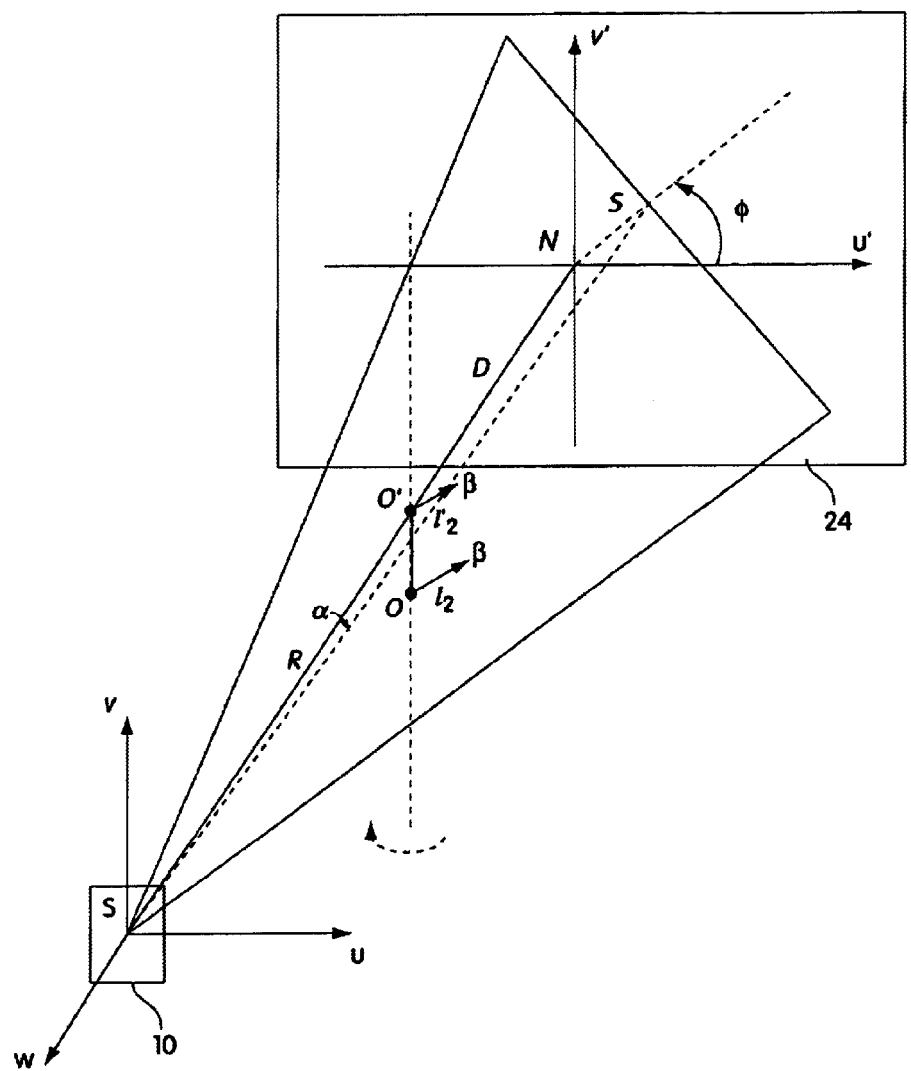
FIG. 19 offers a visualization of how a local basis of a line on the image plane is determined by the global coordinates of a Radon plane as well as a moving basis.

In the subsequent projection, the global coordinates of the plane passing by the next source point $\Phi(\lambda_2)$ and parallel to $L_{l_1,\beta}$ is given by $(l_2, \beta)$, with the same unit normal and $l_2 = \Phi(\lambda_2) \cdot \beta$. Again, we are dealing with lines instead of planes in the subsequent local projection frame. For simplicity, we assume N coincidences with the image center. If the perpendicular line from the source to the detector passes through the global origin, as is the case in the second exemplary embodiment of the detector orientation, the radial distance and the angular variable, $(s, \phi)$, of the intersection line between the plane $L_{l_2,\beta}$ and the second image plane are expressed as $$\begin{cases} s = (R+D) \cdot \frac{l_2}{\sqrt{R^2 - l_2^2}} \\ \phi = \arctan\left(\frac{\beta \cdot v}{\beta \cdot u}\right), \end{cases} \tag{29}$$

in which s is obtained by eliminating $\alpha$ from $\sin \alpha = l_2/R$ and $\tan \alpha = s/(R+D)$ (see FIG. 19).

In the first exemplary embodiment of the detector orientation, there is a slight difference. The perpendicular line from the source to the image plane does not pass through the global center; as a result, the radial distance of the plane $L_{\Phi(\lambda_2)\cdot\beta, \beta}$ shall be offset by $OO' \cdot \beta$. Replacing $l_2$ with $l_2 - OO' \cdot \beta$ in Eqn. (29), we obtain the local coordinates of the intersection line between $L_{l_2,\beta}$ and the second cone-beam image plane.

The second-order Radon transform derivative can therefore be evaluated by subtracting the first-order radial derivative of the Radon transform obtained from two consecutive cone-beam images and dividing by $\Phi(\lambda_2) \cdot \beta - \Phi(\lambda_1) \cdot \beta$. This is essentially the first order approximation through a one-step finite difference. Higher order approximation can be achieved by engaging more cone-beam images. It means that a few more images shall be acquired in advance.

The result is weighted by the multiplicity of each plane intersecting with the source orbit. For the quadratic curve family we have given explicit instructions for finding the number of intersections, as noted before. For a general three-dimensional curve, there is no analytical evaluation of the multiplicity function. Instead of computing and storing the number of intersections for each plane $L_{l,\beta}$ (will be indexed by $(l, \beta)$) with the scan path, one could save computational time and storage by compiling a table for a set of predetermined $\beta$'s. For each $\beta$, a list of l corresponding to the critical points of $\Phi(\lambda) \cdot \beta = l(\lambda)$ is ordered, i.e., $l_1 < l_2 < \ldots < l_{n(\beta)}$ and complied into the table. The multiplicity function is constant within each l-interval, and this value shall also be listed in the table. During the course of image reconstruction, the table can be used to quickly determine the weight of each Radon plane.

Figure 20:
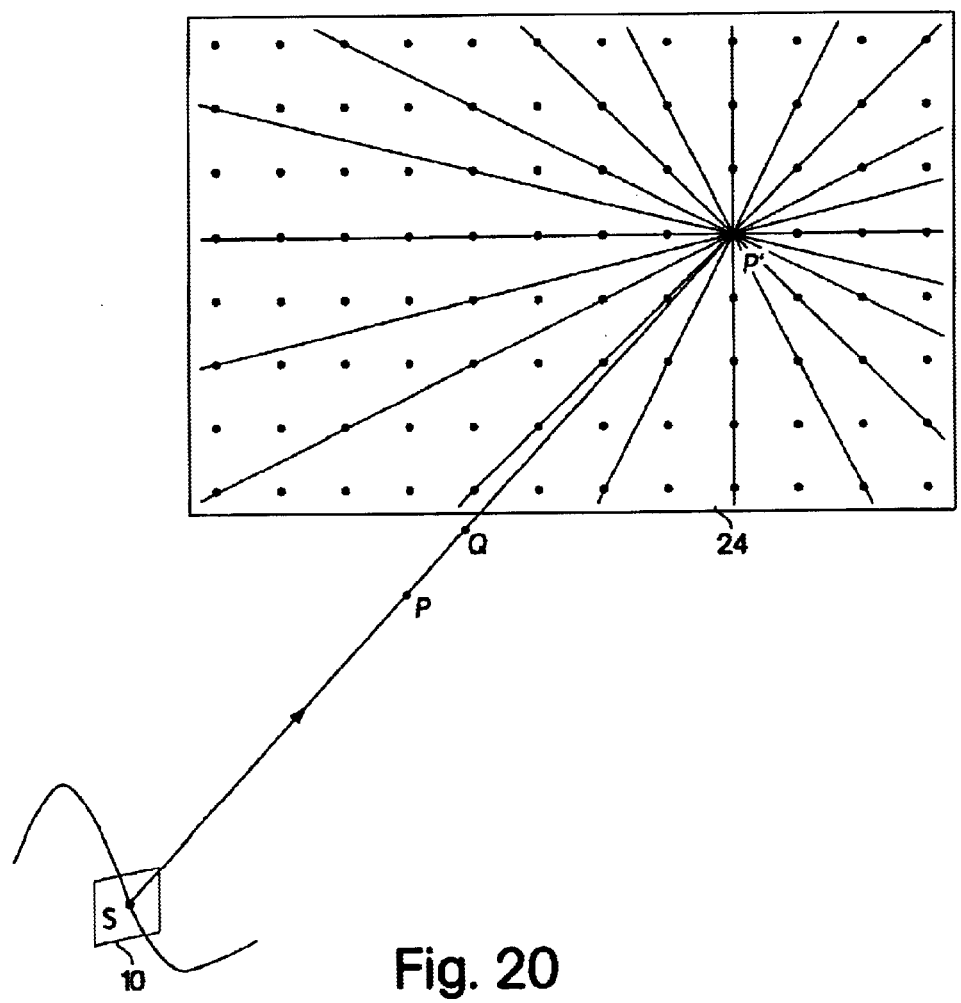
FIG. 20 provides a visualization of sampled planes passing by the same projection line meeting the image plane at a set of rational lines.
Figure 21:
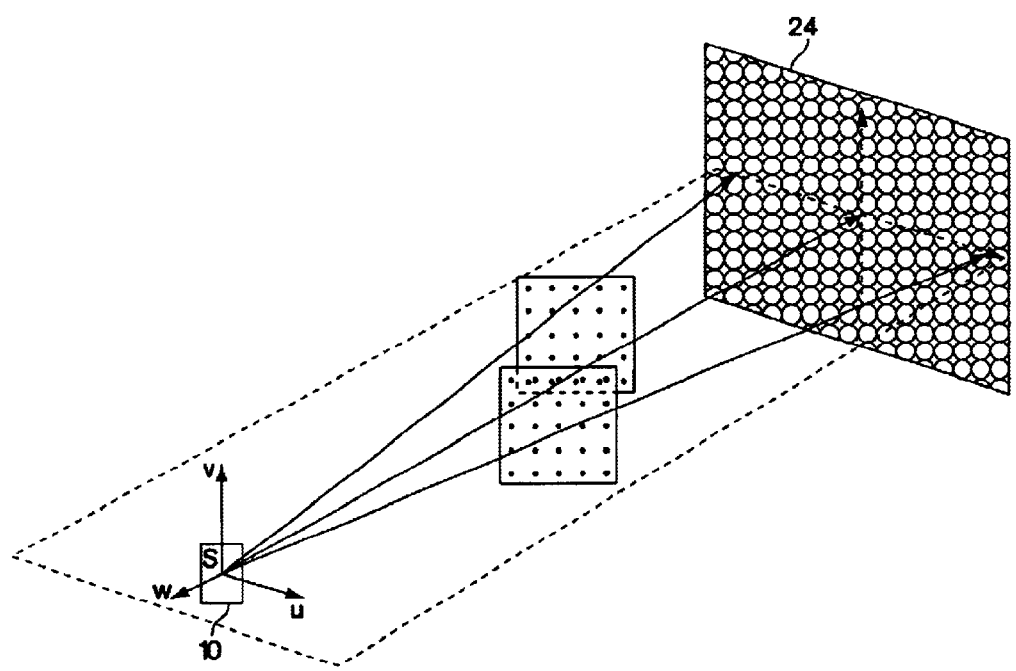
FIG. 21 provides a conceptual image of sampling characteristics of a Cartesian grid that are not aligned with that of the local projection rays.

Now, for each pixel on the image plane, we obtained the second-order radial derivative of the Radon transform on a set of planes corresponding to a set of rational lines passing through the same pixel (see FIG. 20). This discrete data set is then used to approximate the two-dimensional backprojection on the unit circle perpendicular to the projection line from the source to the image pixel by $$\sum_{j=0}^{N-1} R''f(\Phi(\lambda)\cdot\beta_j, \beta_j) \frac{|\Phi'(\lambda)\cdot\beta_j|}{M(\Phi(\lambda)\cdot\beta_j, \beta_j)} \Delta\theta_j \qquad (30)$$

where $\beta_j$'s are unit normal of the processed planes and $\theta_j$'s are the angular intervals between $\beta_j$'s. Note that the $\beta_j$'s and $\theta_j$'s in Eqn. (30), depend only on the scanning geometry (i.e., the scan path and the sampling of scan path) and the geometry of the sampled lines on each cone-beam image plane used to obtained the first-order radial derivative of the Radon transform. The actual attenuation measurement plays no part in determining $\beta_j$'s and $\theta_j$'s. Hence, $\beta_j$'s and $\theta_j$'s can be computed offline prior to the scan and stored in computer-readable media.

For a given pixel on the image plane, the projection line connects this pixel to the source and is constantly valued by the result of the two-dimensional backprojection. The rays emitting from a single source point are projective whereas the object space is represented by a Cartesian grid. As a result, the local and the global coordinates are characterized by different sampling patterns (see FIG. 20). The projection rays are resampled and interpolated to obtain the nodal values on the Cartesian grid. The simplest interpolation scheme is the nearest neighbor method, i.e., finding the closest line for each Cartesian node and assigning the value of its closest neighbor to it. Higher-order approximation can be achieved by involving more neighboring projection lines.

It is clear that the two-dimensional backprojection yields a three-dimensional image. We call the resulting three-dimensional image a local reconstruction because it is reconstructed via differentiating the neighboring cone-beam projection images. Each local reconstruction provides view-dependent information about the object, and it does not recover the variations along each projection line.

The above process is repeated until the cone-beam data acquisition is complete. The ultimate three-dimensional reconstruction is the sum of all the intermediate, locally reconstructed images which can be carried out accumulatively and simultaneously with the scanning and reconstruction process. The final output is a three-dimensional array that can be displayed on a computer screen using proper computer graphics engine, either in the slice-by-slice two-dimensional format or in the form of a computer-rendered three-dimensional anatomical representation. It can also be kept in a storage-media for future use.

The moving frame reconstruction paradigm outlined herein can be applied to general cone-beam imaging systems with a variable choice of scan paths and detector orientations. When applied, minor details may differ (i.e., the construction of a specific moving basis or using different sampling and interpolation schemes, etc.), though the principle that allows accurate and systematic identifying a set of parallel planes via the method of moving frame does not depart.

Helical Cone-Beam Reconstruction

Figure 22:
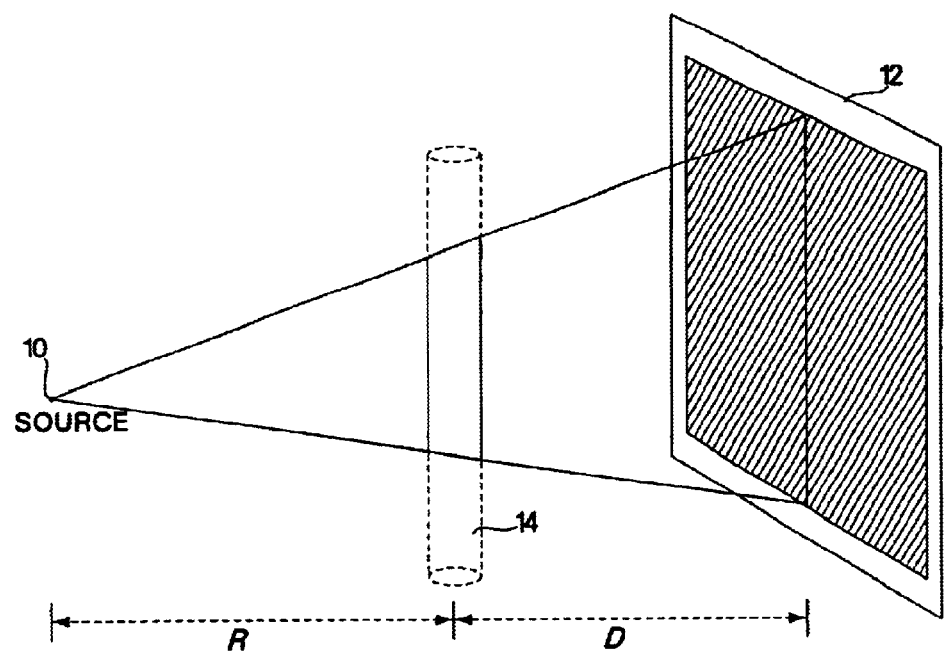
FIG. 22 illustrates a truncated cone-beam projection when the size of the detector is not large enough to receive all of the rays passing through the object.

An important application of cone-beam imaging is the helical cone-beam CT. Data acquisition using a helix as source orbit involves only simple rotation and translation, both in constant speed; thus is easy to implement. In addition, helical cone-beam CT offers a promising solution for scanning long object where detector size is not large enough to capture radiation passing through the entire object inside its field of view (FOV). In the long object case, cone-beam projections outside a finite purview along the axial direction are cut off (FIG. 22). Different parts of the object are scanned sequentially as the source and detector rotate around the object while at the same time moving along the axial direction of the long object.

Figure 23:
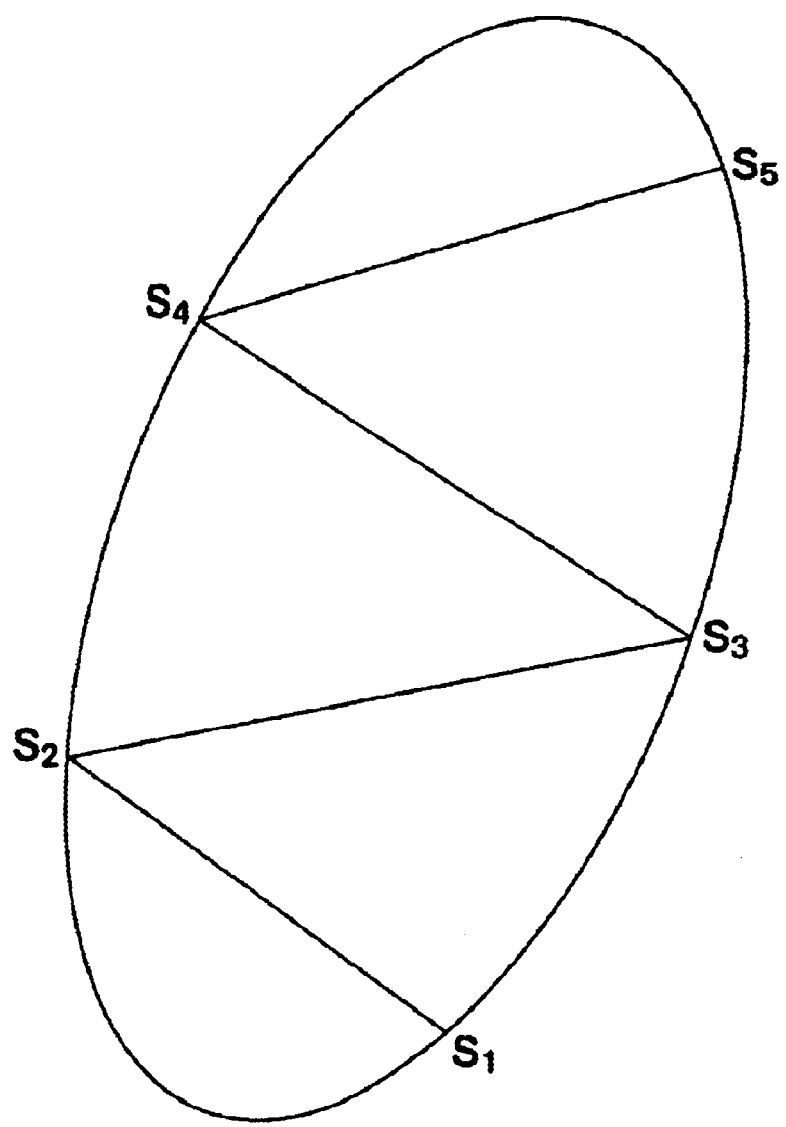
FIG. 23 illustrates a perfect plane triangulation from projections originated at various source points along a helix after applying a Tam-window mask.

The cone-beam imaging method, disclosed above, can be directly applied to non-truncated helical cone-beam CT where the object is completely inside the field of view, and it provides a stable, accurate and near-isotropic solution. When the cone-beam data are axially truncated, which is common in scanning long object, special treatment is needed. In dealing with axially truncated helical cone-beam data, cone-beam image shall be preprocessed by a mask called a Tam-window. According to U.S. Pat. No. 5,504,792, which is incorporated herein by reference in its entirety, for each plane bypassing the object, cone-beams projected from several source points can be patched to form a triangulation of that plane (FIG. 23). These source points are the intersections of the plane with the source orbit, the helix. Note that the intersection of a plane with a cylinder is an ellipse. A perfect triangulation can be achieved when each cone-beam image is masked by the Tam-window. The role of the Tam-window is to eliminate the redundancy in data collection. As a result, the multiplicity function is constantly assigned to 1. The upper boundary of the Tam-window is the projection of the upper helix turn right above the current source point and the lower boundary of the Tam-window is defined by the projection of the lower helix turn right below the current source point.

Figure 24:
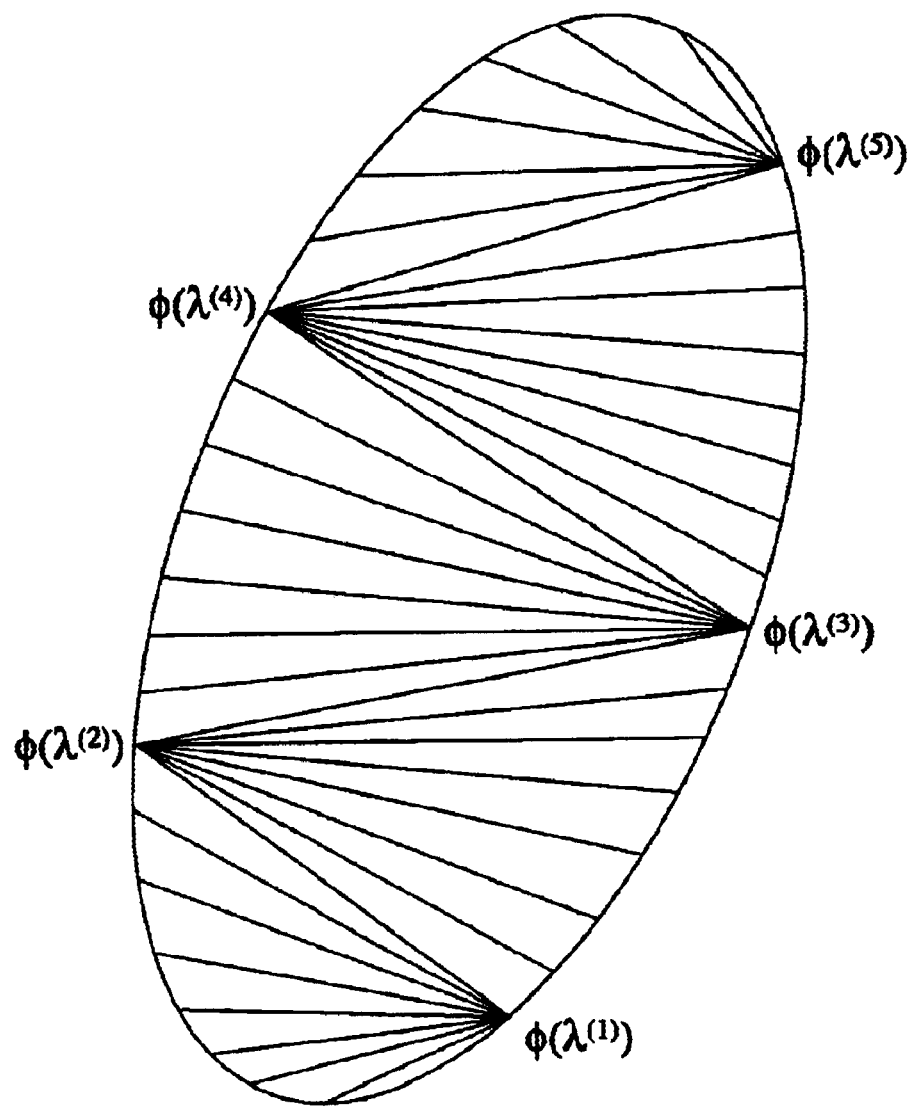
FIG. 24 illustrates the steps of backprojection in the truncated helical cone-beam reconstruction.

Then we follow the reconstruction procedure as previously described: calculating the first-order radial derivative of the Radon transformation, finding the local coordinates of a set of parallel planes in adjacent cone-beam projection frames, calculating the second-order radial derivative of the Radon transform. The departure from the previously described reconstruction is in backprojection. Assume that a cone-beam image is taken at a source point, say $\Phi(\lambda^{(1)})$. In the helical cone-beam reconstruction, the second-order radial derivative obtained for a plane $L_{\Phi(\lambda^{(1)})\cdot\beta,\beta}$, $R''f(\Phi(\lambda^{(1)})\cdot\beta,\beta)$ contributes to the value along the rays (1) originating from $\Phi(\lambda^{(1)})$, (2) lying on plane $L_{101\ (\lambda^{(1)})\cdot\beta,\beta}$, and (c) that have an end inside the Tam-window. $R''f(\Phi(\lambda^{(1)})\cdot\beta,\beta)$ also contributes to the backprojected value along the rays (1) lying on the same plane $L_{\Phi(\lambda^{(1)})\cdot\beta,\beta}$, (2) originating from a few other source points where $L_{\Phi(\lambda^{(1)})\cdot\beta,\beta}$ meets the source orbit (FIG. 24), and (3) are inside the Tam-window in each local projection frame. Denote by $\Phi(\lambda^{(i)})$ (i=2,3, ..., M ($\Phi(\lambda^{(1)})\cdot\beta,\beta$)) the set of plane-helix-intersections. Since source orbit is sampled, we have only finite number of source points. The sampled source points may not coincide with the intersections. Let $\Phi(\lambda^{(i)'})$ denote the nearest point to $\Phi(\lambda^{(i)})$ (i=2,3, ..., M ($\Phi(\lambda^{(1)})\cdot\beta,\beta$)) on the sampled source orbit. From Eqn. (25), the additive contribution of $R''f(\Phi(\lambda^{(1)})\cdot\beta,\beta)$ to each projection line through $\Phi(\lambda^{(i)'})$ and on the plane $L_{\Phi(\lambda^{(i)})\cdot\beta,\beta}$ can be approximated by $R''f(\Phi(\lambda^{(1)})\cdot\beta,\beta)|\Phi(\lambda^{(i)'})\cdot\beta^{(i)}|\Delta\theta^{(i)}$, where $\beta^{(i)}$ is the normal vector of a plane and is nearest to $L_{\Phi(\lambda^{(i)})\cdot\beta,\beta}$, processed in the local frame originating at $\Phi(\lambda^{(i)'})$, $\Delta\theta^{(i)}$ is the angular interval as in Eqn. (25) and it is also calculated in the local frame originating at $\Phi(\lambda^{(i)'})$. After backprojection, the same procedure is repeated for consecutive cone-beam images collected. The intermediate results are accumulated to produce the final reconstruction.

While this invention has been shown and described with references to particular embodiments thereof, those skilled in the art will understand that various changes in form and details may be made therein without departing from the scope of the invention, which is limited only by the following claims.

What is claimed is:

1. A method for generating a three-dimensional image of a scanned object from a plurality of cone-beam projections passed through the object and attenuated thereby, the method comprising:
   a) positioning a source at a position on a predetermined scan path;
   b) passing a projection of cone-beam radiation comprising a plurality of projection rays from the source through an object, the cone-beam projection being attenuated by partial absorption in the object;
   c) detecting radiation intensity of the attenuated cone-beam projection on an area detector;
   d) obtaining a two-dimensional attenuation image of the cone-beam projection from the detected radiation intensity;
   e) obtaining an intermediate transform function from the two-dimensional attenuation image on a set of planes passing through the source; then
   f) repeatedly:
      i) displacing the source to another position on the predetermined scan path and then
      ii) repeating steps (b)–(e);
   g) filtering the intermediate transform functions acquired from consecutive attenuation images at two or more source positions using a moving-frame technique to obtain the second-order radial derivative of the Radon transform;
   h) backprojecting the second-order radial derivative of the Radon transform in a two-dimensional space along each projection ray passing through a source position among the source positions referenced in step (g) to generate an intermediate, locally reconstructed, three-dimensional image with constant values assigned along each projection ray;
   i) at least once, repeating steps (f)–(h); and
   j) summing the plurality of intermediate, locally reconstructed, three-dimensional images obtained for the plurality of cone-beam projections to obtain an ultimate, reconstructed, three-dimensional image of the object.

2. The method of claim 1, wherein the predetermined scan path is everywhere differentiable with exception allowed at a finite number of points.

3. The method of claim 1, wherein the intermediate transform function is the first-order radial derivative of the Radon transform.

4. The method of claim 3, wherein each two-dimensional attenuation image is obtained as a discrete two-dimensional data set with an area detector comprising a plurality of detector elements, and wherein the step of obtaining the first-order radial derivative of the Radon transform includes:
   i) interpolating data points lying between grid nodes along a set of virtual image lines;
   ii) calculating a weighted sum of attenuation along each virtual image line with weights determined by the cosine of the angle between (a) a projection ray associated to an image point and (b) a central ray, which is the shortest line from the source to the virtual image line;
   iii) differentiating the weighted sum over a set of parallel virtual image lines to obtain the first-order radial derivative of the Radon transform on a set of corresponding planes passing through the source; and
   iv) storing the resulting first-order radial derivative of the Radon transform in memory for use in a subsequent phase of reconstruction.

5. The method of the claim 4, wherein, if the area detector does not coincide with the standard image plane, the method further comprises:
   a) mapping the coordinates of the detector elements to the coordinates of a set of points on a standard image plane under a projective coordinate transform; and
   b) interpolating the two-dimensional data set to obtain attenuation values on a regular grid on the standard image plane.

6. The method of claim 4, wherein the virtual image lines pass through a set of grid nodes on a standard image plane, wherein the same number of virtual image lines of different slopes passing through each grid node, and wherein the collection of slopes of the intersecting virtual image lines is the same at each grid node.

7. The method of claim 4, wherein the regular grid has square or rectangular elements.

8. The method of claim 1, wherein the two-dimensional backprojection along a projection ray is an integral over all planes passing by that ray, wherein the unit normal vectors of these planes are confined to a great circle on the unit sphere.

9. The method of claim 1, wherein a plurality of cone-beam projections are successively passed through the object, and wherein the step of determining the second-order radial derivative of the Radon transform includes:
   i) determining the global coordinates, represented by the unit normal and radial distance, of a set of corresponding planes pass though a set of virtual image lines on the standard image plane and through the current focal point;
   ii) obtaining the first-order radial derivative of the Radon transform on a set of planes for the next one or more cone-beam projections;
   iii) calculating the local parameters of intersection image lines between standard image planes in successive cone-beam projections and corresponding planes in successive cone-beam projections parallel to the set of planes passing through the current focal point via a coordinate transformation determined by a moving-frame technique;
   iv) interpolating the first-order radial derivative of the Radon transform for the planes obtained in part (iii) from the first-order radial derivative of the Radon transform obtained in part (ii); and
   v) obtaining the second-order radial derivative of the Radon transform by differentiating, which can be approximated by a finite difference, the first-order radial derivative of the Radon transform over the parallel planes from consecutive cone-beam projections.

10. The method of claim 1, wherein the step of backprojecting the second-order radial derivative includes:
   for each projection ray associated with a node on the image plane, calculating a weighted sum of the second-order radial derivative of the Radon transform over a set of planes passing through the projection ray with weights determined by (a) the number of intersections of each plane with the scan path, (b) the absolute value of a dot product between a tangent vector of the scan path at the current source position and a unit normal vector of the plane, and (c) the angular interval between two adjacent planes;
   multiplying the weighted sum by an incremental value of the source orbit parameter, $\lambda$, from the current source position to a next source position;

assigning the resulting value to points lying on the projection ray; and resampling and interpolating the projection rays so that each node on a three-dimensional Cartesian grid representing the object is positioned on one of the rays and is assigned a value to produce a three-dimensional, locally reconstructed image.

11. The method of claim 1, wherein the radiation is X-ray radiation.

12. The method of claim 1, wherein the detector is aligned according to at least one of the following:

a) the detector is placed orthogonal to a line connecting the source to the global-coordinate origin, and an axis of the detector is aligned with the projection of the tangent of the scan path at a current source position onto the detector; and b) the detector is place with a first axis parallel with a rotational axis of the scan path and a second axis parallel with a projection of the tangent of the scan path at a current source position onto a plane perpendicular to the rotational axis of the scan path.

13. The method of claim 1, wherein the moving frame technique involves the generation of a set of orthonormal bases with the origin of each orthonormal basis positioned at the source such that each time the source is repositioned and the two-dimensional attenuation image is obtained, the orthonormal basis has a new origin, wherein the moving frame technique enables locating a set of parallel planes from consecutive cone-beam projections and enables the second-order radial derivative of the Radon transforms to be evaluated by filtering over the set of parallel planes from consecutive cone-beam projections.

14. The method of claim 13, wherein the moving frame technique enables location of the planes in a subsequent cone-beam projection parallel to the set of planes in the current projection via a set of coordinate transforms, the method further comprising:

i) for each selected line on a current standard image plane, finding global coordinates, which can be expressed as l and $\beta$, in the Radon space of a corresponding plane passing through a focal point of the cone-beam radiation and intersecting the standard image plane at the selected line;

ii) finding global coordinates, which can be expressed as l and $\beta$, of planes passing through the focal point of the subsequent cone-beam projection and parallel to the planes obtained in part (i), wherein two parallel planes have the same unit normal but different radial distances from the global origin; and iii) finding local coordinates, which can be expressed as polar coordinate, s and $\phi$, on a standard image plane, of intersection lines between the planes obtained in part (ii) and a standard image plane of the subsequent cone-beam projection.

15. The method of claim 1, wherein the source and the detector are attached to a rigid arm that is mounted to a rotary motor that axially rotates the rigid arm.

16. The method of claim 15, wherein the rigid arm includes one or more slides to which the source and detector are attached, the slides displacing the source and detector along an axis parallel to the axis of rotation of the rigid arm.

17. The method of claim 15, wherein the object is displaced along the axis of rotation of the rigid arm.

18. The method of claim 2, wherein the detector is not large enough to detect the entirety of a projection of radiation passing from the source through the entirety of the object.

19. The method of claim 18, wherein the predetermined scan path is a helical scan path; and the detected radiation is masked using a Tam window to eliminate redundancy, wherein backprojecting the second-order radial derivative further comprises an extra step of adding a contribution of the second-order radial derivative on processed planes to reconstructions at other source points that pass through the same plane, the extra step including:

for every plane where the second order radial derivative of the Radon transform is evaluated, finding a set of intersections between the plane and the helical scan path, which can be denoted by $\Phi(\lambda^{(i)})$ (i=2,3, ..., $M(\Phi(\lambda^{(1)}) \cdot \beta, \beta))$, where $\Phi(\lambda)$ is the parameterized scan path, $\beta$ is the unit normal of the said plane and $M(\Phi(\lambda^{(1)}) \cdot \beta, \beta)$ is the multiplicity function which equals the number of the intersections of the plane and the helical scan path;

finding the source points nearest to $\Phi(\lambda^{(i)})$ (i=2,3, ..., $M(\Phi(\lambda^{(1)}) \cdot \beta, \beta))$, which can be denoted by $\Phi(\lambda^{(i)'})$ (i=2,3, ..., $M(\Phi(\lambda^{(1)}) \cdot \beta, \beta))$, on the sampled scan path; and adding a contribution of the evaluated second-order radial derivative on the plane, which can be denoted by $R''f(\Phi(\lambda^{(1)}) \cdot \beta, \beta)$, to each projection line passing through $\Phi(\lambda^{(i)})$ i=2,3, ..., $M(\Phi(\lambda^{(1)}) \cdot \beta, \beta)$, and on the plane through $\Phi(\lambda^{(i)'})$ and having unit normal $\beta$, wherein the amount of contribution can be approximated by $R''f(\Phi(\lambda^{(1)}) \cdot \beta, \beta)|\Phi(\lambda^{(i)}) \cdot \beta^{(i)}|\Delta\theta^{(i)}$, where $\beta^{(i)}$ is the normal vector of a plane (a) nearest to the plane through $\Phi(\lambda^{(i)'})$ and having unit normal $\beta$; (b) being evaluated in the local frame originating at $\Phi(\lambda^{(i)'})$, where $\Delta\theta^{(i)}$ is the angular interval between neighboring planes evaluated in the local frame originating at $\Phi(\lambda^{(i)'})$ and passing the projection line.

20. A cone-beam tomography apparatus comprising a radiation source, a radiation detector, a support for an object to be scanned by radiation from the radiation source, a computer-readable storage medium storing computer-executable software for generating a reconstruction of cone-beam radiation attenuation in an object, the software comprising:

code for obtaining an intermediate transform function on a set of planes from a signal representing the amount of radiation transmitted through the object;

code for determining the second-order radial derivative of the Radon transform by filtering the intermediate transform function over a set of parallel planes using a moving-frame technique;

code for backprojecting the second-order radial derivative of the Radon transform to generate an intermediate, locally reconstructed, three-dimensional image with constant values assigned along each projection ray;

code for summing the plurality of intermediate, locally reconstructed, three-dimensional images obtained for the cone-beam projections to obtain an ultimate, reconstructed, three-dimensional image of the object; and code for displacing the source and detector relative to the support in a predetermined scan path for radiation transmitted from the source, through an object positioned by the support, and to the detector.

21. The apparatus of claim 20, wherein the predetermined scan path is everywhere differentiable with exception allowed at a finite number of points.

22. The apparatus of claim 20, further comprising a rigid arm to which the source and the detector are attached.

23. The apparatus of claim 22, wherein the rigid arm is mounted to a rotary motor to allow the rotary motor to axially rotate the rigid arm.

24. The method of claim 23, wherein the rigid arm includes one or more slides to which the source and detector are attached, the slides allowing displacement of the source and detector along an axis parallel to the axis of rotation of the rigid arm.

* * * * *